United States Patent [19]

Grahn

[11] Patent Number: 5,726,520

[45] Date of Patent: Mar. 10, 1998

[54] DIRECT DRIVE FIELD ACTUATOR MOTORS

[75] Inventor: Allen R. Grahn, Salt Lake City, Utah

[73] Assignee: Bonneville Scientific Incorporated, Salt Lake City, Utah

[21] Appl. No.: 482,201

[22] Filed: Jun. 7, 1995

Related U.S. Application Data

[63] Continuation-in-part of Ser. No. 101,496, Aug. 2, 1993, Pat. No. 5,432,395.

[51] Int. Cl.⁶ .................................................. H01L 41/08
[52] U.S. Cl. .................................... 310/328; 310/323
[58] Field of Search ................................ 310/323, 328

[56] References Cited

U.S. PATENT DOCUMENTS

| | | | |
|---|---|---|---|
| 4,019,073 | 4/1977 | Vishnevsky et al. | 310/323 |
| 4,613,782 | 9/1986 | Mori et al. | 310/323 |
| 4,782,262 | 11/1988 | Kiyo-Oka | 310/323 |
| 4,975,614 | 12/1990 | Honda | 310/323 |
| 5,079,471 | 1/1992 | Nygren, Jr. | 310/328 |
| 5,191,252 | 3/1993 | Sano | 310/328 |
| 5,205,147 | 4/1993 | Wada et al. | 310/328 |
| 5,241,235 | 8/1993 | Culp | 310/328 |
| 5,266,863 | 11/1993 | Nonami et al. | 310/328 |
| 5,410,207 | 4/1995 | Miura et al. | 310/328 |
| 5,416,375 | 5/1995 | Funakubo et al. | 310/323 |
| 5,424,597 | 6/1995 | Gloss et al. | 310/328 |
| 5,432,395 | 7/1995 | Grahn | 310/328 |
| 5,465,021 | 11/1995 | Visscher et al. | 310/328 |

*Primary Examiner*—Mark O. Budd
*Attorney, Agent, or Firm*—Trask, Britt & Rossa

[57] ABSTRACT

A positive-drive field actuator motor including a stator carrying at least one field actuator which changes in dimension responsive to application of an energy field, and at least one drive shoe movable by the dimensional changes of the field actuator to contact and move a rotor element with respect to the stator. Various embodiments of the motor are disclosed, and the rotor element may be moved linearly or arcuately.

9 Claims, 24 Drawing Sheets

|  | a | b | c | d | e | f | g | h |
|---|---|---|---|---|---|---|---|---|
| PZA 272 | E | 3/4 E | 1/2 E | 1/4 E | NE | 1/4 E | 1/2 E | 3/4 E |
| PZA 270 | 1/2 E | 3/4 E | E | 3/4 E | 1/2 E | 1/4 E | NE | 1/4 E |
| SHOE DIRECTION | D & R | D | U & R | U | U & L | U | D & L | D |
| ELEMENT DIRECTION | R | R | R | NM | NM | NM | NM | NM |

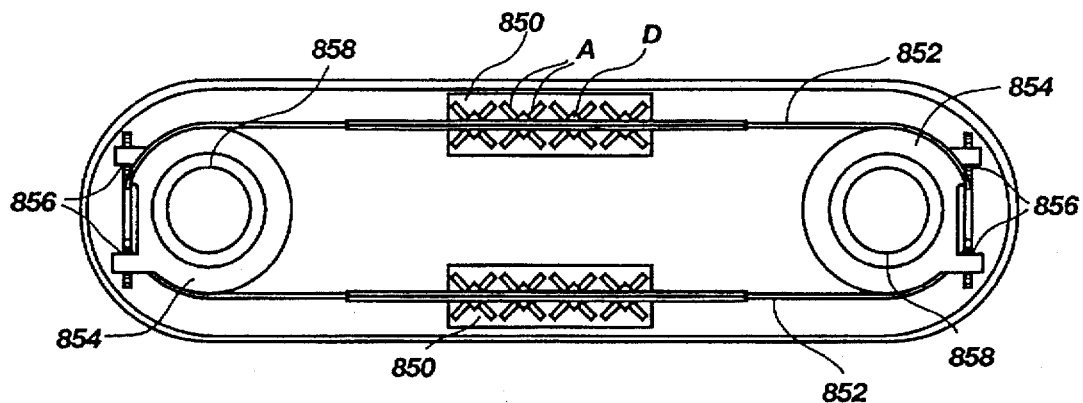
Fig. 35
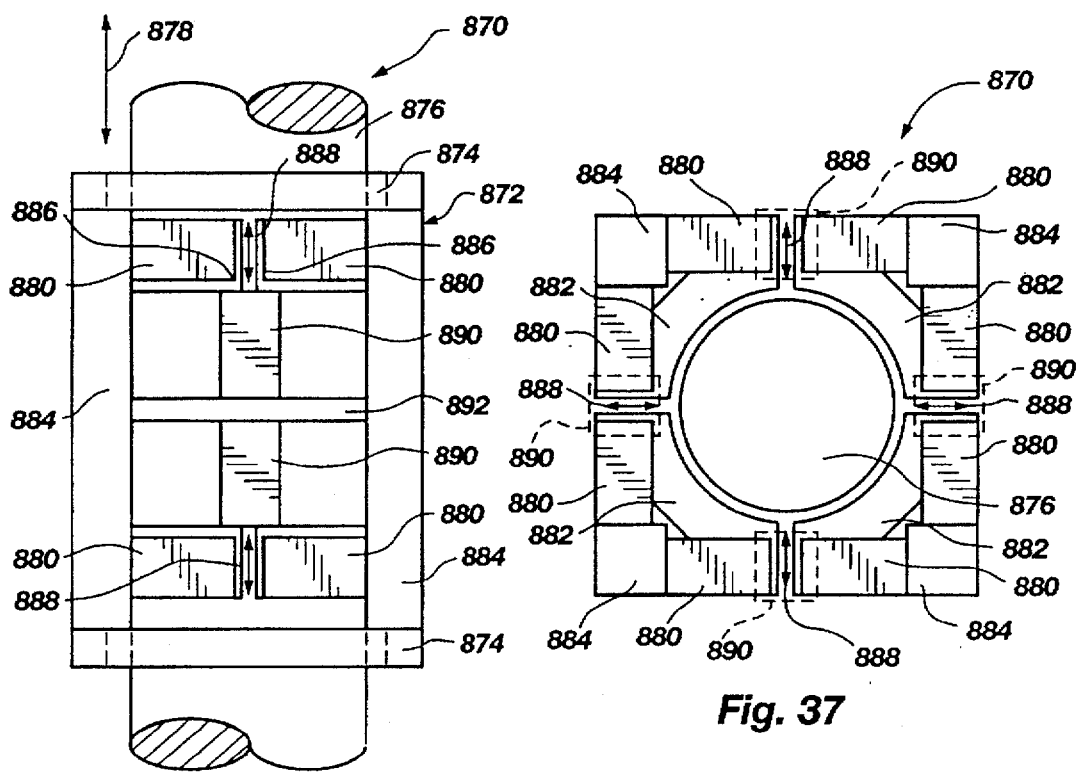
Fig. 36
Fig. 37

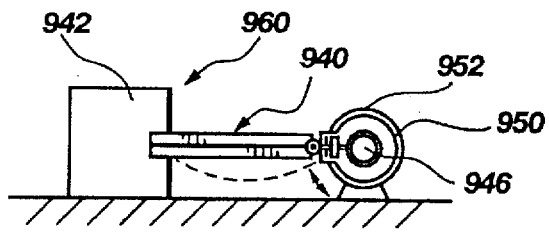
Fig. 44
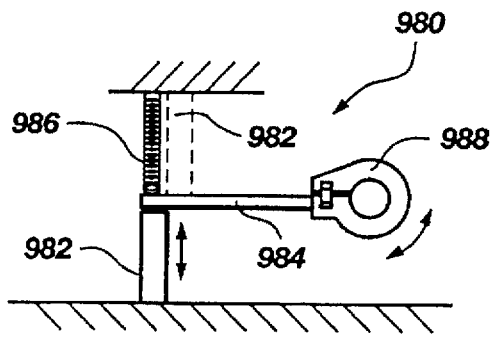
Fig. 46
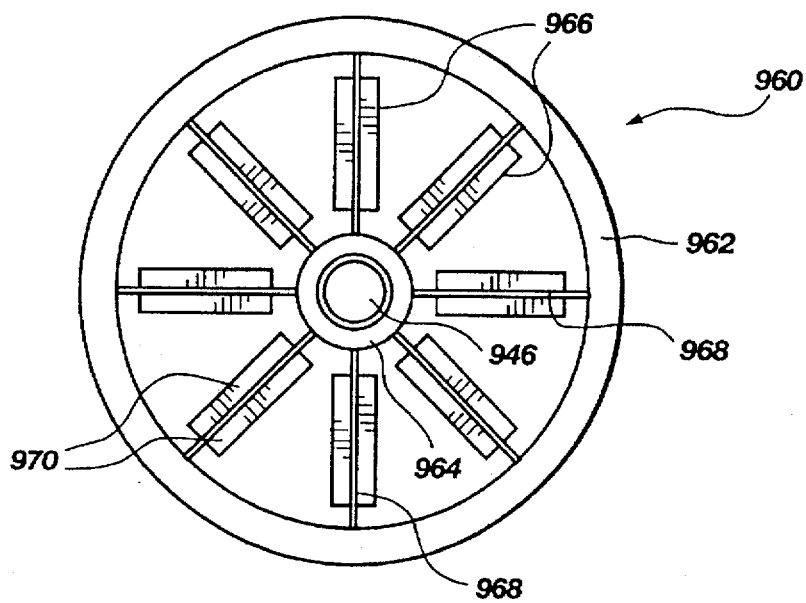
Fig. 45
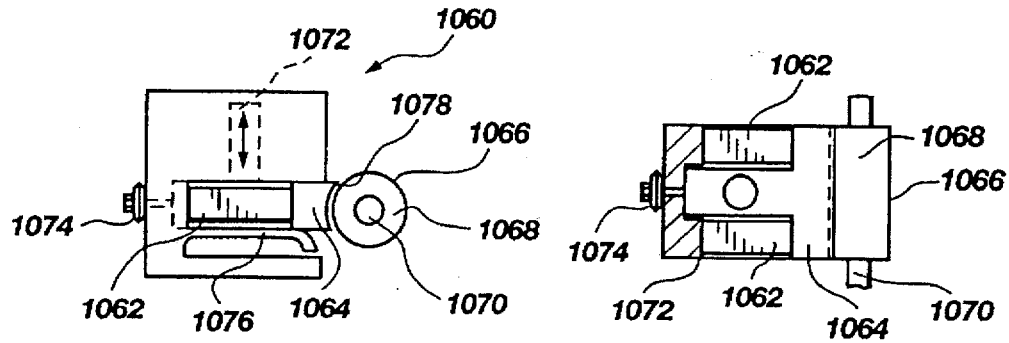
Fig. 54
Fig. 55

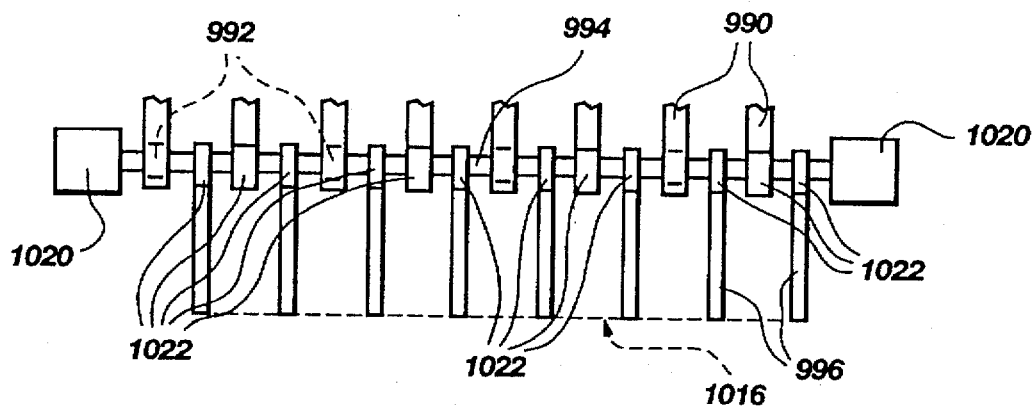
Fig. 49
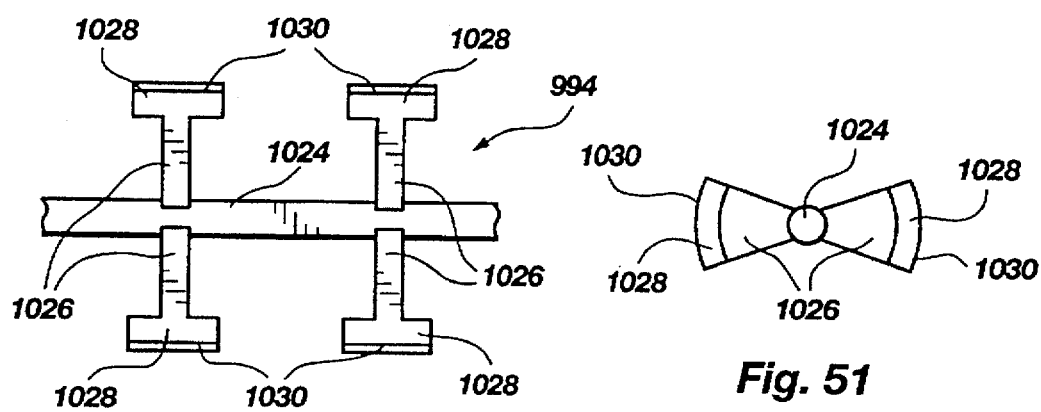
Fig. 50
Fig. 51
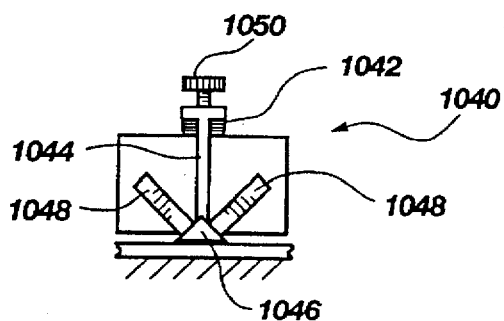
Fig. 52
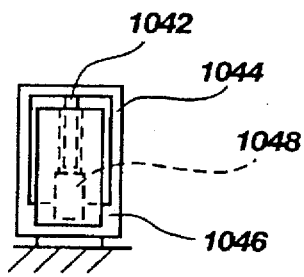
Fig. 53

DIRECT DRIVE FIELD ACTUATOR MOTORS

This is a continuation-in-part of U.S. patent application Ser. No. 08/101,496 filed Aug. 2, 1993, now U.S. Pat. No. 5,432,395.

RIGHTS OF UNITED STATES GOVERNMENT

This invention was made with Government support under Contract No. DE-FG02-92ER81439 awarded by the Department of Energy. The Government has certain rights in the invention.

This invention was made with Government support under Contract Nos. NAS8-38914, NAS8-39362 and NAS7-1205 awarded by the National Aeronautics and Space Administration. The Government has certain rights in the invention.

BACKGROUND OF THE INVENTION

1. Field of the Invention

The present invention relates generally to motors, and more specifically to piezoelectric and other field actuator motors employing motive power elements which physically elongate, bend or otherwise change dimensions responsive to changes in electrical or magnetic fields.

2. State of the Art

Traditional electric motors cause a shaft or rotor to rotate by creating a magnetic field between a primary winding in a stationary portion, or stator, of the motor and a secondary winding associated with the shaft or rotor. Such motors are relatively large and heavy relative to output torque. Such motors for many applications, must be connected to transmission systems that alter speed and torque output and, in some instances, convert the rotary movement of the motor rotor to linear movement. These transmission systems, however, add substantially to the size, weight and complexity of the motors. Altering the electrical power input to such motors also provides some adjustability of output, but in most instances such adjustability is limited in range and, as with transmission systems, adds bulk, complexity and cost to the motor system.

Various other types of electric motors have been developed that employ piezoelectric, magnetostrictive, or electrostrictive actuators as motive power elements, rather than magnetic attraction or repulsion as in traditional electric motors. A piezoelectric actuator has a first length when a first voltage (or electric field) is applied across it and a second length when a second voltage is applied across it. An electrostrictive actuator has a first length when a first voltage is applied across it and a second length when a second voltage is applied across it. A magnetostrictive actuator has a first length when a first magnetic field is applied to it and a second length when a second magnetic field is applied to it. As used herein, a term "field actuator" may refer to a piezoelectric, magnetostrictive, or electrostrictive actuator.

It is also contemplated that piezoelectric and other field actuators configured as "bending" actuators in structures which behave similar to bimetallic strips employed in thermostats are also encompassed by the term "field actuator," as are shape memory alloy structures exhibiting similar dimensional variances in response to temperature fluctuations. Therefore, it may also be suitable to characterize the term "field actuator" as encompassing structures adapted to vary in at least one dimension responsive to application or removal of any energy field.

Motors employing piezoelectric actuators as motive power elements have been used in the prior an to create linear and rotary movement. For example, U.S. Pat. No. 5,027,027 to Orbach et al. describes a linear motor referred to as an "Inchworm" motor that includes forward, center, and rear piezoelectrically activated cylindrical elements arranged about a shaft. The shaft is moved forward, for example, by clamping the forward element, extending the center element, clamping the rear element, and releasing the forward element.

U.S. Pat. No. 4,578,607 to Tojo et al. describes a system in which piezoelectric actuators move sections to rotate a disk. The disk is lowered onto the sections after which they are moved by the actuators. The disk is then raised while the actuators reset. Some actuators elongate during the time other actuators contract.

SUMMARY OF THE INVENTION

The present invention provides a unique, compact, high torque, variable speed motor adaptable to continuous or incremental movement, either linear or rotary, of a directly driven motor element.

The motor of the present invention is easily configured for a variety of applications, including fingers and thumbs of robotic hands, limb joints in a variety of robotic designs, electromechanical control systems and other uses where high torque or with precision displacement control is desirable, as well as in traditional motor applications where small size, low weight and reliability are constraining design factors.

The motor of the present invention, as presently contemplated by the inventor and not by way of any limitation on other embodiments which may in the future fall within the ambit of the claims appended to this specification, is a stepper motor which may be structurally configured to perform as a "finger motor", a "star motor" or a "ratchet motor." All of the embodiments of the invention disclosed herein employ for motive power dimensional changes induced in field actuators (as previously defined herein) responsive to periodic fluctuations of electrical, magnetic or other energy fields, to drive linearly or rotationally movable elements, sometimes referred to herein as "rotors."

The finger motor, so called because of its ready applicability to use in digits of robotic or prosthetic hands, employs at least two mutually rotationally movable segments. A selectively energized first field actuator is employed as the motive power element for a clamping means for locking one segment to a rotatable driven element, and a selectively energized second field actuator is employed with the other segment as the motive power element for engaging the rotatable driven element when the first field actuator is energized to activate the clamping means. To provide more power and to effectuate substantially continuous movement by the rotated segment, two counter-rotating drive actuators may be employed, each periodically energized at the appropriate time in cooperation with a cooperating clamping actuator as will be hereinafter described.

The star motor, so called because of the resemblance of a rotary embodiment thereof in side or plan elevational view to a many-pointed star, employs as motive power elements one or more pairs of field actuators carried by a stator assembly to periodically drive a drive element or shoe against a resilient restraint in a rotational, ellipsoidal trajectory against a driven rotor element, which rotor element may in fact move rotationally or linearly, the term "rotor" being used only in the descriptive sense of identifying the element being moved with respect to the stator assembly. Depending upon the particular orientation desired, each of the field actuators of the pair may be oriented at an oblique angle to the surface of the rotor engaged by the drive shoe (hereinafter termed a "V-drive" motor), or one may be oriented substantially perpendicular to the rotor surface and one substantially parallel thereto (hereinafter termed an "L-drive" motor). Selective energizing and de-energizing of one or both actuators at appropriate times and for appropriate intervals, the exact sequence depending upon whether a V-drive or an L-drive is employed in the motor, results in the drive shoe engaging the rotor, translating in the direction of desired rotor movement and subsequently disengaging from the rotor and moving back to its starting position with respect to the actuators. Other actuator orientations and motor configurations are also disclosed.

The ratchet motor, so called due to the manner in which one or more drive field actuators act upon the rotor, is in some respects similar to the finger motor in that one or more field actuator-controlled clamping means are employed in combination with one or more drive actuators to transmit linear drive actuator movement to the rotor.

It should be understood and appreciated that the motor of the present invention may in many instances be fabricated by using existing parts of an assembly to be motorized. For example, in any rotating joint, there will normally be bearing means and a shaft interposed between structural members. By modifying the existing structure to accept actuators, and adding a few additional parts, a motor according to the present invention can be easily fabricated. The compactness of field actuators and their extremely high power density, in combination with the drive systems forming a part of the present invention, results in motors that can be very small and light relative to torque output, and which for the vast majority of preferred applications do not require a transmission.

BRIEF DESCRIPTION OF THE DRAWINGS

FIG. 35 is a schematic side elevation of a tandem V-drive linear star motor employing flexible strips or bands as rotor elements;

FIGS. 36 and 37 comprise, respectively, schematic top and end elevations of a compact linear motor employing actuator-driven clamping and drive assembly elements;

FIG. 44 is a schematic side elevation of a rotational shaft drive structure employing a bending PZA in combination with split-ring PZA clamping structures as employed in the ratchet motors of FIGS. 25 and 26;

FIG. 45 is a schematic side elevation of a rotational shaft drive structure employing a plurality of bending PZA's arranged in a spoke pattern about a tubular PZA clamping sleeve engageable with a shaft extending therethrough;

FIG. 46 is a schematic side elevation of a rotational shaft drive structure employing a linearly-expandable PZA acting upon a lever arm which is selectively engaged with the shaft via a clamping structure;

FIGS. 49, 50 and 51 are, respectively, a schematic top elevation of a torsionally driven aircraft flap adjustment structure employing PZA clamping mechanisms, and of enlarged segments of the torsionally-driven shaft employed therewith;

FIGS. 52 and 53 comprise, respectively, side and end elevations of V-drive linear motors employing a cradle-type drive shoe support and adjustable, compression-type biasing mechanisms; and FIGS. 54 and 55 comprise, respectively, side and partial sectional top elevations of a rotational drive mechanism employing linear PZA actuator-driven movement to engage a shaft with a drive shoe, in combination with coordinated transverse PZA actuator-driven movement of the drive shoe opposed by a biasing element to effect shaft rotation.

DETAILED DESCRIPTION OF THE ILLUSTRATED EMBODIMENTS

As noted previously, the present invention contemplates at least three types of motor embodiments, which for convenience are referred to herein as a "finger motor," a "star motor," and a "ratchet motor." None of these motors requires a transmission for reducing a high rotor speed to enhance torque output, as in conventional electric motors, but instead may be termed a "direct drive" motor with respect to the digit, limb, valve or other structure to which the rotor is secured or engaged. The motor embodiments are hereafter discussed in detail in the above order of reference.

A. Finger Motor

The finger motor received its name because its applications include use in robotic or artificial human (prosthetic) fingers. The finger motor uses one or more oscillating drive structures and one or more oscillating clamping structures to cause one segment on the finger motor to rotate with respect to another segment, similar to the way one segment of a human finger rotates with respect to another segment about a knuckle joint. The term "oscillating" as used herein denotes a structure including an element which may be selectively caused, responsive to application of an appropriate electrical, magnetic or other energy field, to change in at least one dimension such as length or width, or to change in shape (for example, to bend), and to return to its original dimension or shape responsive to the removal of the field or to application of a field of opposite polarity. Such changes, induced on a periodic basis, are employed to drive the motors of the present invention.

Described in terms analogous to electrical terminology, the finger motors of the present invention may be described as mechanical rectifiers which employ a single direction of the back-and-forth motion of expanding and contracting field actuators to develop large linear or rotational motion of a driven motor element.

1. A First Preferred Embodiment

FIGS. 1-6 illustrate a first preferred embodiment of a finger motor according to the present invention.

Figure 1:
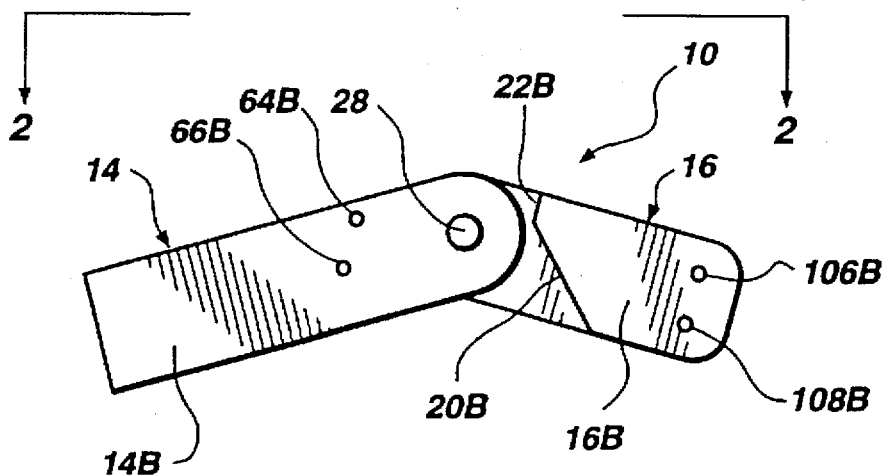
FIG. 1 is a side elevation of a finger motor assembly according to a first preferred embodiment of the present invention.

FIG. 1 shows a side view of a finger motor assembly 10, including a first segment 14 and a second segment 16, which is rotatably secured to segment 14 and, as disclosed, rotates with respect to segment 14 as motor 10 operates. (It is assumed that segment 14 is held stationary so that segment 16 rotates. Alternatively, segment 16 could be held stationary, so that segment 14 would rotate.) Segment 14 includes two oscillating drive structures and segment 16 includes two oscillating clamping structures.

Segment 16 includes a ridge 20B that ultimately limits clockwise movement of segment 16 (as viewed in FIG. 1) with respect to segment 14 and a ridge 22B that limits counterclockwise movement of segment 16 with respect to segment 14. The shapes and positions of ridges 20B and 22B may be changed as desired to allow different limitations on the range of clockwise and counterclockwise movement of segment 16 relative to segment 14.

Figure 2A:
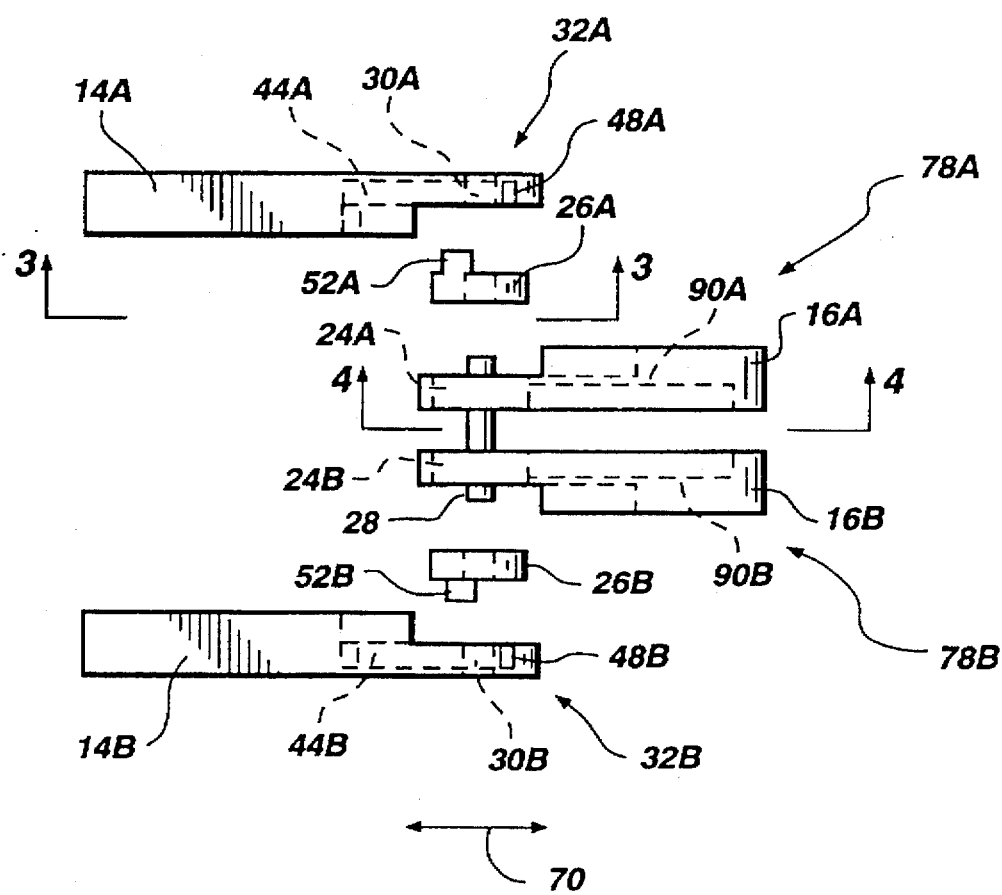
FIG. 2A is an exploded top elevation of the finger motor assembly of FIG. 1 as viewed from line 2—2 of FIG. 1.
Figure 2B:
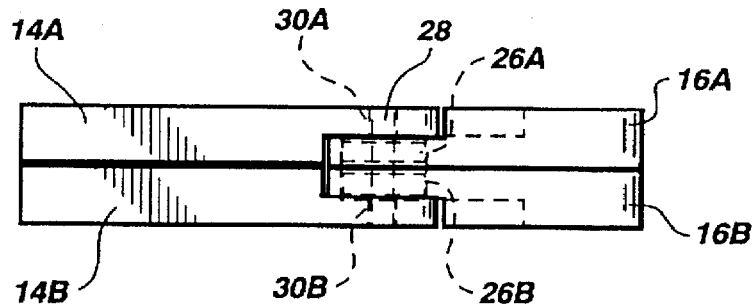
FIG. 2B is a top elevation of the finger motor assembly as viewed from line 2—2 of FIG. 1.
Figure 2C:
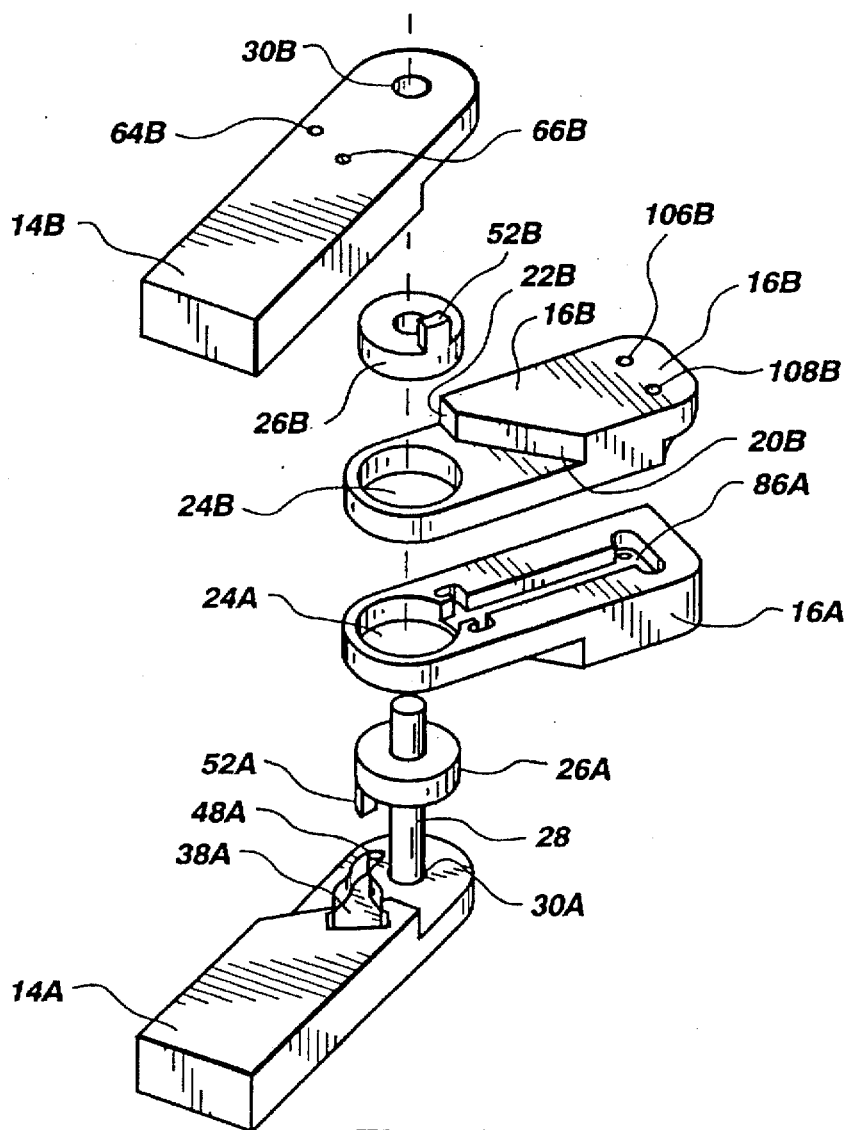
FIG. 2C is a perspective view of a portion of the finger motor assembly of FIG. 2B.

FIG. 2A shows an exploded top view of finger motor assembly 10 as viewed from line 2—2 of FIG. 1. FIG. 2B shows a top view of finger motor assembly 10 as viewed from line 2—2 of FIG. 1. For convenience in construction and assembly of finger motor 10, segment 14 may be comprised of subsegments 14A and 14B, which are manufactured separately and joined together at final assembly. Likewise, segment 16 may be comprised of subsegments 16A and 16B, which are manufactured separately and joined together at final assembly. The subsegments may be joined together to form a segment by pins, screws, brackets, adhesive, or other conventional means known in the art. Subsegment 14A is the mirror image of subsegment 14B. Subsegment 16A is the mirror image of subsegment 16B, except as noted hereafter with respect to the orientation of the oscillating drive structure carried thereby in a modification of the preferred embodiment. In this description and in the drawing figures, a reference number followed by the letter "B" identifies a component which is the same as or generally a mirror image of a component identified with the same reference number followed by the letter "A." For example, subsegment 16A includes exterior ridges 20A and 22A (not shown), which are the mirror images of ridges 20B and 22B.

Subsegments 16A and 16B include aligned bushing cavities 24A and 24B, which cavities have diameters that are slightly large than the diameter of rotary drive elements comprising bushings 26A and 26B. A cylindrical rod, such as knuckle pin 28, extends through bushings 26A and 26B retained in bushing cavities 24A and 24B, and is secured at each end by means known in the art in pin receptacles 30A and 30B in segments 16A and 16B, respectively. Bushings 26A and 26B freely rotate within bushing cavities 24A and 24B, and about knuckle pin 28. A shim or spacer (not shown) may separate segments 14A and 14B when assembled as segment 14 of finger motor 10, in order to provide appropriate clearance for movement of segment 16 with respect thereto.

Figure 3:
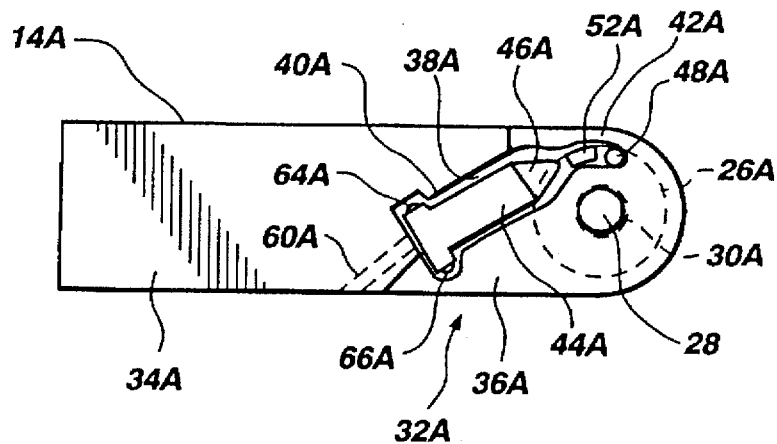
FIG. 3 is a side view of a drive subsegment of the finger motor assembly as viewed from line 3—3 of FIG. 2A.

Oscillating drive structures 32A and 32B are described in connection with FIG. 3, which shows a side view of subsegment 14A viewed from line 3—3 of FIG. 2A. Referring to FIG. 3, subsegment 14A includes parallel but laterally offset surfaces 34A and 36A, as well as a slot 38A, which is formed in surface 36A. Slot 38A includes a major portion 40A shaped to hold a piezoelectric or other field actuator (hereinafter referred to generically as a "PZA") 44A of similar configuration, and an arcuate minor portion 42A into which extends drive shoe 46A adjacent to PZA 44A. Minor slot portion 42A also receives at its distal end an elastic or otherwise resilient return member 48A, and drive pin 52A which extends laterally from bushing 26A (lines) at the periphery thereof (see FIG. 2A) into minor slot portion 42A between drive shoe 46A and return member 48A. In this first embodiment, oscillating drive structure 32A includes PZA 44A, drive shoe 46A and return member 48A. Completing the description of subsegment 14A, a threaded hole 60A aligned with the longitudinal axis of PZA 44A receives a screw (unnumbered) used to adjust the position of PZA 44A in major slot portion 40A. So that expansion of PZA will result in movement of drive shoe 46A against drive pin 52A. A shim may be placed between the screw and PZA 44A. Holes 64A and 66A receive wires from a control circuit 74, shown in FIG. 5, to apply a control signal to drive PZA 44A.

The control or drive signal applied to PZA 44A may be selected from a variety of waveforms such as, by way of example and not limitation, a sinusoidal wave, a triangular wave, a square wave, or a rectangular-shaped wave. When the voltage of the control signal increases from a voltage V1 (which may be zero volts or "ground", or even a negative voltage) to a voltage V2, the length of PZA 44A increases so as to move drive shoe 46A against drive pin 52A in the clockwise direction against elastic return member 48A, compressing the latter. Of course, bushing 26A rotates with movement of drive pin 52A, and when segment 16 is clamped to bushing 26A as hereinafter described, segment 16 will rotate with bushing 26A. When the voltage of the control signal decreases from voltage V2 to voltage V1, the length of PZA 44A decreases and the stored energy in compressed return member 48A moves drive pin 52A in the counter-clockwise direction. The parameters of PZA 44A and its driving waveform, and elastic member 48A are chosen so bushing 26A rotates between clockwise and counter-clockwise directions.

Oscillating drive structure 32B includes PZA 44B, drive shoe 46B and return member 48B, these and the other elements comprising segment 14B being substantially identical in material and configuration to those corresponding elements previously described with respect to segment 14A. Use of a second oscillating drive structure 32B thus provides for continuous driving of segment 16 as, while drive structure 32A is being "reset" by contraction of PZA 44A and movement of bushing 26A by return member 48A, drive structure 32B is driving segment 16 via bushing 26B in a ratchet-like phenomenon. It will be appreciated that distal segment 16 may be counter-rotated back to its initial position by using the force of elastic return members 48A and 48B and re-timing the clamping structures 78A and 78B accordingly, as hereinafter described. Alternatively, the clamping structures may merely be de-energized, and segment 16 may then swing freely about knuckle pin 28 with respect to segment 14. This feature is contemplated as having utility if it is desired to withdraw a robotic hand from an obstructed passage. The driving waveform for PZA 44B would normally be substantially identical to that for PZA 44A.

Another alternative for positive counter-rotation is to reorient slot 38B in segment 14B to drive bushing 26B in a counterclockwise direction responsive to elongation of PZA 44B. With reference to FIG. 3 of the drawings, the orientation of slot 38B in the direction of drive in such modification would be described as downward and to the right, in contrast to the drive direction of slot 38A would be described as upward and to the right. Thus, bushing 26B will, like bushing 26A, be caused to rotate between counter-clockwise and clockwise directions. However, unlike bushing 26A, movement of bushing 26B in the counter-clockwise direction will be caused by an increase in the length of PZA 44B and movement in the clockwise direction will be caused by the stored energy of compressed elastic return member 48B.

Figure 4:
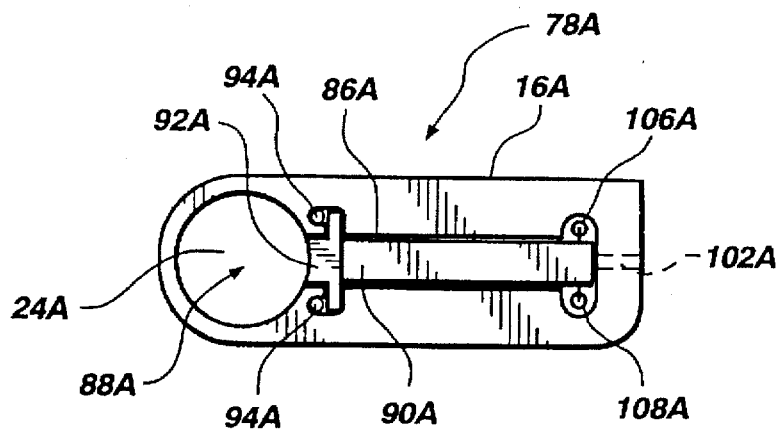
FIG. 4 is a side view of a clamp subsegment of the finger motor assembly as viewed from line 4—4 of FIG. 2A.

Oscillating clamping structures 78A and 78B are described in connection with FIGS. 2A and 2B, and FIG. 4, which shows a side view of subsegment 16A viewed from line 4—4 of FIG. 2A. Referring to FIG. 4, subsegment 16A includes previously referenced bushing cavity 24A, which has a diameter that is slightly larger than the diameter of bushing 26A. Subsegment 16A also includes a slot 86A, which is preferably oriented in alignment with a radial line from the center 88A of bushing cavity 24A and shaped to hold a PZA 90A and a clamping shoe 92A adjacent to PZA 90A. In this first embodiment, clamping structure 78A includes PZA 90A and clamping shoe 92A. Clamping structure 78B includes PZA 90B and clamping shoe 92B.

A threaded hole 102A receives a screw used to adjust the position of PZA 90A. A shim may be placed between the screw and PZA 90A. Holes 106A and 108A receive wires from control circuit 74 to apply a control signal to drive PZA 90A.

As with PZA 44A the control or drive signal applied to PZA 90A may be selected from a variety of exemplary waveforms such as a sinusoidal wave, a triangular wave, a square wave, or a rectangular-shaped wave, but in practice no particular waveform is required, since clamping PZA 90A is either "on" or "off."

However, if a square wave is employed as the control or drive signal PZA 90A, it is preferred that a resistance be placed in series with the actuator to slow down the speed of the wave form during the energizing portion of the cycle, to reduce impact forces between components, with attendant wear and noise reduction.

When the voltage of the control signal increases from a voltage V3 (which may be zero volts or even a negative voltage) to a voltage V4, the length of PZA 90A increases so as to move damping shoe 92A against bushing 26A with sufficient force so that subsegment 16A locks with bushing 26A (i.e., subsegment rotates if bushing 26A rotates and does not rotate if bushing 26A does not rotate). Voltages V3 and V4 may, in fact, correspond to V1 and V2. When the voltage of the control signal decreases from voltage V4 to voltage V3, the length of PZA 90A decreases so that shoe 92A does not press against bushing 26A with significant force and segment 16A does not rotate with bushing 26A. As with oscillating drive structures 32, one or more elastic return members 94A may easily be incorporated into clamping structure 78 to positively bias clamping shoe 92A against PZA 90A and to reduce the force applied by clamping shoe 92A against bushing 26A when PZA 90A is in its contracted state.

As previously noted, segment 16B is a mirror-image twin of segment 16A, and the oscillating clamping structure 78 is substantially identical to structure 78B. As with PZA 90A, the control signal applied to PZA 90B controls whether clamping shoe 92B does or does not press against bushing 26B with a force sufficient to cause segment 16B to lock with bushing 26B.

Figure 5:
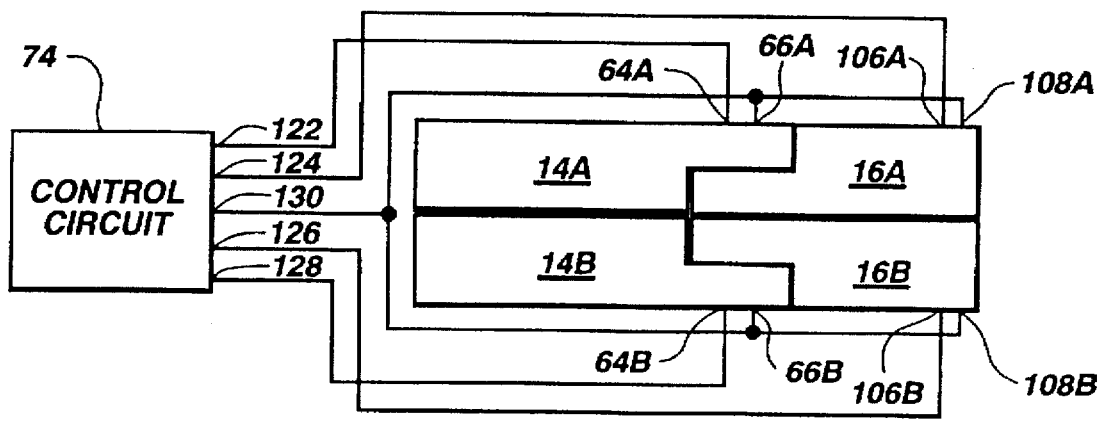
FIG. 5 is a partial schematic view of a control circuit and interconnections to piezoelectric actuators employed in the finger motor assembly of FIG. 1.

Referring to FIG. 5, control circuit 74 (which may be characterized as an energy source to drive the field actuators) is connected to PZA's 44A, 44B, 90A, and 90B through conductors such as wires, which are preferably secured to the sides of segments 14 and 16. Control circuit 74, which may be generally termed the piezoelectric motor drive electronics, is designed to produce phased voltage waveforms such as the square waveforms depicted in FIG. 6. Applied voltage may commonly range from −40V to +500V, depending upon the particular actuator selected. Digital logic circuitry is employed to generate logic-level pulses, the timing of which can be easily adjusted, as the circuitry employs shift registers and counters driven by a system clock, all as known in the art. The clock is preferably a function generator so that clock frequency fluctuations may be employed to alter motor speed proportionally. Low voltage logic-level pulses drive the gates of MOSFETS, which in turn apply the control signals to the actuators. A resistor is employed in series with the actuator leads to decouple the capacitive load of the actuators and to limit the current during both energizing and de-energizing of the actuators.

All of the aforementioned components being commercially available and assembly thereof into a workable control circuit 74 being well within the ability of one of ordinary skill in the art, no further description of control circuit 74 except as to its function will be made. It should be understood that control circuit 74 does not form a part of the present invention, except insofar as it provides suitably shaped and timed signals to energize and de-energize the PZA's. Control circuit 74 may respond to real-time control by external control devices, for example directly tracking the movement of a human operator's fingers, or may be preprogrammed to operate in a variety of sequences. In either instance, such control methodology is known in the art and forms no part of the present invention. It will be appreciated and understood by those of ordinary skill in the art that field actuators other than the piezoelectric type may require a modified control circuit or energy source, but such modification is easily effected and is within the ability of those skilled in the art.

Control circuit 74 includes outputs 122, 124, 126, 128, and 130. Output 130 provides a ground potential. The control signal applied to PZA 44A is delivered to outputs 122 and 130, which are connected to PZA 44A by conductors passing through holes 64A and 66A. The control signal applied to PZA 90A is delivered to outputs 124 and 130, which are connected to PZA 44A by electrical conductors (such as wires) passing through holes 106A and 108A. The control signal applied to PZA 44B is delivered to outputs 128 and 130, which are connected to PZA 44B by conductors passing through holes 64B and 66B. The control signal applied to PZA 90B is delivered to outputs 126 and 130, which are connected to PZA 90B by conductors passing through holes 106B and 108B.

The rotation of segments 16A and 16B with respect to segments 14A and 14B, and thus the operation of finger motor assembly 10, is induced and controlled as follows. When it is desired that segments 16A and 16B rotate in the clockwise direction, PZA 90A is energized during the time bushing 26A is to be caused to rotate in the clockwise direction by the expansion of PZA 44A, and PZA 90B is then energized in conjunction with PZA 44B to rotate bushing 26B while bushing 26A is released from segment 16 and rotates counterclockwise. It is noted that bushing 26A turns through a very small arc, for example 0.15°–0.3°, during each expansion of PZA 44A, although the expansion of PZA 44A in a human-finger sized motor provides a relatively large force, typically 21 kg. Therefore, finger motor 10 may be described as a high-torque, low-speed motor. When it is desired that segments 16A and 16B rotate in the counterclockwise direction, PZA 90B is energized during the time bushing 26B is to be caused to rotate in the counterclockwise direction by expansion of PZA 44B, and PZA 90A is not energized, except as described below.

Figure 6:
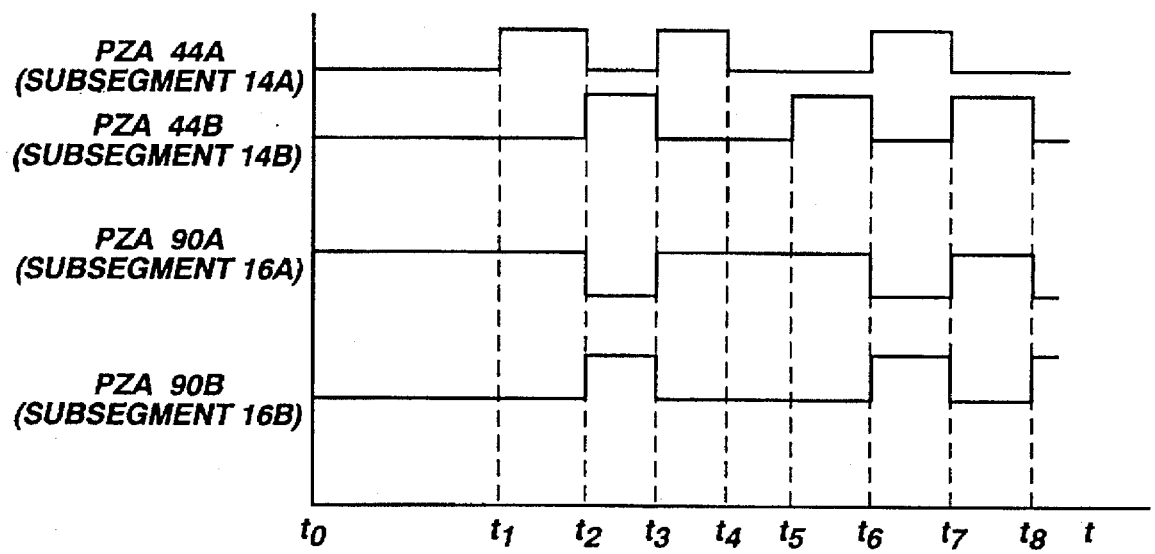
FIG. 6 is graphically representation of a preferred sequence of energized and de-energized states of the actuators employed in the finger motor assembly of FIG. 1.

FIG. 6 graphically illustrates a preferred sequence of energized and de-energized states of PZA's 44A, 44B, 90A, and 90B using square wave control signals for controlling the position of segment 16. In FIG. 6, the x-axis represents time and the y-axis represents whether PZA's 44A, 44B, 90A, and 90B are in the energized or de-energized state, the de-energized states being represented by the corresponding wave form baselines, and the fully energized states by the tops of the square waves.

From time t0 to time t1, control circuit 74 determines that segment 16 should not rotate. Therefore, from time t0 to time t1, the state of PZA's 44A and 44B remains constant. To prevent gravity from pulling segment 16 rotationally downward about knuckle pin 28, at least one of PZA's 90A and 90B (e.g., PZA 90A) should be energized to lock a bushing to segment 16, rotation thereby being prevented by the limited travel of the bushing's drive pin. It should be noted that more than adequate locking torque to prevent rotation of segment 16 is available from PZA 90A, and that if more is required a larger PZA may be employed, or both PZA 90A and 90B may be energized.

Shortly before time t1, control circuit 74 determines that segment 16 should rotate in the clockwise direction from time t1 to time 14. Accordingly, from time t1 to time 14, PZA 44A alternates between energized and de-energized states, as does PZA 44B, which is energized during alternate periods to those in which PZA 44A is energized. PZA 90A should be energized and PZA 90B should be de-energized during the time PZA 44A is energized and causes drive shoe 46A to move drive pin 52A and thus cause bushing 26A to turn clockwise. PZA 44A remains energized until time t2, which corresponds to the time at which bushing 26A stops rotating clockwise and elastic return member 48A is fully compressed. To prevent gravity from pulling segment 16 rotationally downward, there should be no time or essentially no time during which PZA 90A and PZA 90B are both de-energized. At about time t2, there is a short period of time during which bushing 26A has essentially no clockwise or counter-clockwise movement. PZA 90B is energized and PZA 90A is de-energized during this short period of time. It is preferred under some circumstances that PZA 90B be energized before PZA 90A is de-energized so as to prevent segment 16 from rotating counterclockwise responsive to the expansion of elastic return member 48A when PZA 44A is de-energized.

However, this requirement is dependant upon several factors. For example, at lower frequencies (such as 500 Hz or less) of energization pulses or waves for PZA 44, there may be a greater tendency or opportunity for segment 16 to rotate counter to the intended direction of movement due to gravity or other loads, as well as to return forces of elastic return member 48A when PZA 44A is de-energized. However, the reversal of movement direction of segment 16 responsive to expansion of return member 48A can be minimized by appropriate early timing of the de-energization of PZA 90A and release of changing shoe 92A as PZA 44A nears the extent of its expansion. Operation of finger motor 10 at higher frequencies (for example, above 1 kHz) reduces slippage due to loading on segment 16 as the drive strokes of drive shoe 46A occur in such rapid succession, so that energization of PZA 90B prior to de-energizing PZA 90A may be necessary only under high load conditions.

From about time t2 to about time t3, bushing 26A freely rotates in the counter-clockwise direction under the return force of elastic member 48A. However, PZA 90B is energized as is PZA 44B, so bushing 26B, and segment 16, again rotate in the clockwise direction to the limit of travel of drive pin 52B, at which time, about t3, PZA 44B is de-energized. At about time t3, there is a short period of time during which both bushings 26A and 26B have essentially no clockwise or counter-clockwise movement. PZA 90A is energized and PZA 90B is de-energized during this short period of time. Again, as noted above, that PZA 90A may or may not be energized before PZA 90B is de-energized, to prevent slippage of segment 16 with respect to segment 14.

At about time t3 and subsequent to energization of PZA 90A, PZA 44A is energized causing bushing 26A to again rotate clockwise. PZA 44A remains energized until time t4, which corresponds to the time at which bushing 26A stops rotating clockwise because elastic member 48A is fully compressed. During the same period, bushing 26B freely rotates counter-clockwise since PZA 90B has been de-energized. At about time t4, there is a short period of time during which bushings 26A and 26B have essentially no clockwise or counter-clockwise movement. PZA 90B would again be energized and PZA 90A de-energized during this short period of time in preparation for energization of PZA 44B to drive bushing 26B.

However, at time t4, control circuit 74 determines that segment 16 should rotate counter-clockwise from time t5 to time t8 and determines that PZA 90A should remain energized to lock segment 16 in place. Then, from time t5 to time t8, again PZA 44B alternates between energized and de-energized states with PZA 44A. However, to achieve counter-clockwise rotation of segment 16, PZA 90B and PZA 90A should each be energized during the time its associated bushing 26A or 26B is turned counter-clockwise responsive to the return force of the stored energy in a return member 48A or 48B. PZA 44B remains energized from time t5 to time t6, which corresponds to the time at which bushing 26B (and segment 16) stops rotating counter-clockwise because elastic member 48B is fully compressed. At about time t6, there is a short period of time during which bushing 26B has essentially no clockwise or counter-clockwise movement. PZA 90B is then energized and PZA 90A is de-energized during this short period of time, and bushing 26B and segment 16 are rotated in a counter-clockwise direction by return member 48B. From about time t6 to about time t7. Also during time t6 to t7, PZA 44A is energized to load return member 48A. At about time t7, there is a short period of time during which bushing 26B has essentially no clockwise or counter-clockwise movement. PZA 90A is then energized and PZA 90B is de-energized during this short period of time, and bushing 26A and segment 16 rotated in a counter-clockwise direction.

At about time t7, PZA 44B is energized, causing bushing 26B to rotate counter-clockwise. PZA 44B remains energized until time t8, which corresponds to the time at which bushing 26B (and segment 16) stops rotating clockwise because elastic member 48B is fully compressed. At about time t8, there is a short period of time during which bushing 26B has essentially no clockwise or counter-clockwise movement. PZA 90B is energized and PZA 90A is de-energized during this short period of time, and bushing 26B and segment 16 are rotated counter-clockwise.

The piezoelectric actuators which comprise the motive power elements in the preferred embodiments of the invention are polycrystalline ceramic materials such as barium titanate and lead zirconate titanate. Such piezoelectric ceramics must be poled for the piezoelectric phenomenon to occur, and such process being well known in the art it will not be described herein.

In order to form an actuator, it is common to stack a large member of individual ceramic wafer elements is series and to then wire the elements in parallel. The longer or higher the stack, the greater the displacement of the actuator when it is energized. Piezoelectric actuators are now commercially available to produce strains of almost 0.1% at voltages as low as 100V, and greater strains at higher voltages have been observed. Such actuators possess individual layers of about 0.1 mm thickness, the layers consolidated by a high pressure solid sintering process.

Characteristics of two suitable piezoelectric actuators of different size and dimensions are set forth below:

| Size | 2 mm × 3 mm × 9 mm | 2 mm × 3 mm × 18 mm |
| --- | --- | --- |
| Max. Voltage | 100 v | 100 v |
| Displacement | 6.5 microns/100 v. | 15 microns/100 v |
| Generated Force | 21 kg | 21 kg |
| Self Resonant Freq. | 150 kHz | 75 kHz |
| Static Capacitance | 175 nF | 400 nF |
| Dissipation Factor | 3.5% | 3.5% |
| Number of Layers | 64 | 144 |
| Compressive Strength | 9000 kg/cm2 | 9000 kg/cm2 |
| Tensile Strength | 50 kg/cm2 | 50 kg/cm2 |
| Mass | 0.5 g | 0.9 g |

The smaller actuators are suitable for use as drive PZA's, while the larger ones have been found useful as clamping PZA's, in human-sized robotic fingers.

Piezoelectric actuators suitable for use in finger motor 10 as well as in other embodiments of the invention are commercially available, by way of example and not limitation, from NEC, Tokyo, Japan; Tokin Corporation, Tokyo, Japan; Sensor Technology Limited, Collingwood, Ontario, Canada; and Dr. Lutz Pickelmann, Piezomechanik Optik, Munich, Federal Republic of Germany. Such actuators, as with substantially all PZA's, develop maximum force at zero displacement and zero force at maximum displacement.

Such actuators at temperatures below about 150° C. have a high resistance, on the order of $10^{11}$ ohms. Thus, under static operating conditions (after expansion) virtually no current is drawn nor power consumed in maintaining a state of activation. In other words, if it is desired to immobilize the digits of a robotic or prosthetic hand in a particular position, the power draw is negligible, a major advantage when using portable or otherwise limited electrical power sources.

It was also discovered that applications of voltages to certain PZA's suitable for use in the present invention from a negative range (rather than for zero volts or ground) increased the actuator elongation or displacement achieved, and suitable circuitry may be employed to take advantage of this known phenomenon if desired.

It is notable that, in an application such as powering digits or "fingers" of human-sized robotic hands, the additional mass of incorporating piezoelectric motors according to the present invention into the fingers may be less than 10 grams per joint or segment, inclusive of all necessary components as described above. Of course, larger actuators are available and might be incorporated in scaled-up, much larger hands for handling heavy objects.

Materials for the finger motor according to the present invention may be selected according to the contemplated operating environment, but ideally should be, in general, light and strong. For example, segments 14 and 16 may be of high strength aluminum, bushing 26 and knuckle pin 28 of steel or stainless steel. More exotic segment materials include titanium, and bushings may be machined from a variety of alloys as known in the art, such as brass, beryllium copper or Inconel® metal.

Elastic return members 48A may be coil springs, elastomeric stops or plugs, leaf or torsion springs, Belleville washers, or other means known in the art.

2. Alternative Preferred Embodiments

As previously noted, the invention may employ field actuators other than PZA's, such as magnetostrictive or electrostrictive actuators.

Figure 7:
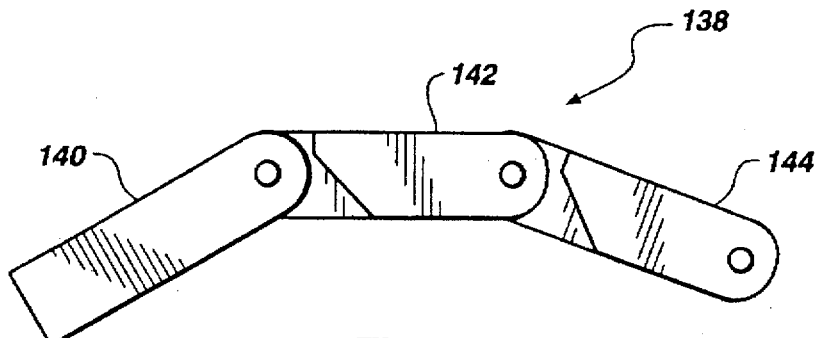
FIG. 7 schematically illustrates a three-segment finger motor according to the present invention.
Figure 8:
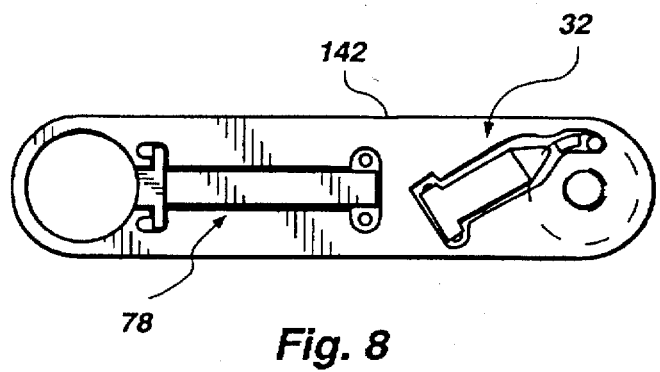
FIG. 8 shows a segment having both a drive structure and a clamping structure, suitable for employment in at least the middle segment of the three-segment finger motor of FIG. 7.

The finger motor may have more than two segments. For example, FIG. 7 shows a three-segment mechanical finger motor 138 having segments 140, 142, and 144. Basal segment 140 may be held stationary allowing proximal segment 142 and distal segment 144 to rotate. Proximal segment 142 may include both oscillating drive structures 32 and clamping structures 78, as schematically shown, for example, in FIG. 8, so as to have the ability to move responsive to an oscillating drive structure in basal segment 140, and to move distal segment 144 having a clamping structure.

Figure 9:
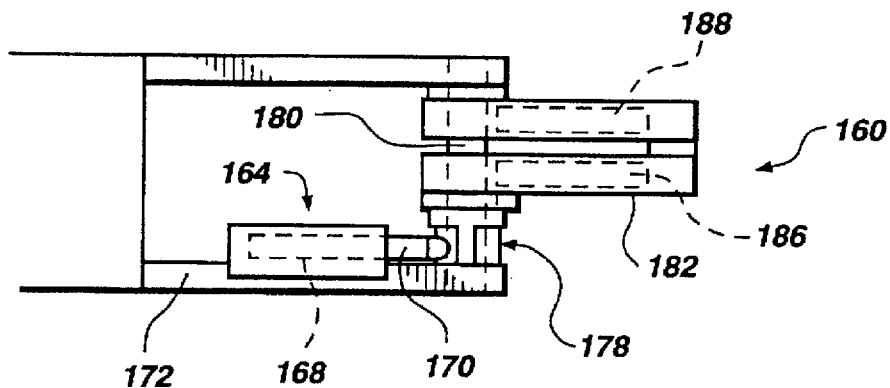
FIG. 9 is a top view of an alternative embodiment of a finger motor according to the present invention.
Figure 10:
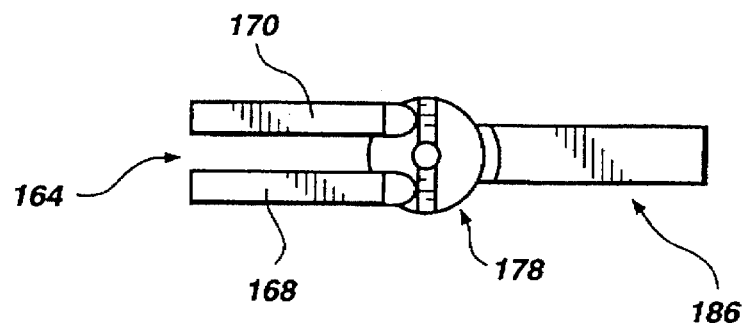
FIG. 10 is a side or plan view of the finger motor drive structure of FIG. 9.

FIGS. 9 and 10 show an alternative embodiment of finger motor employing a positive, rather than resilient or elastic, return for the rotator bushing. A finger motor 160 includes an oscillating drive structure 164, which includes two PZA's 168 and 170 and is supported by a support 172. PZA's 168 and 170 alternately expand to push against a rotator 178 rotationally mounted on a fixed shaft 180 to which distal segment 182 is attached. Two oscillating clamping structures 186 and 188 are employed. Activation of structures 186 and 188 are timed so that the rotating, distal segment 182 moves distal segment 182 in a clockwise direction by activation of PZA 170 and clamping of rotator 178 by clamping structure 186, distal segment being subsequently locked in place on shaft 180 by clamping structure 188 when rotator 178 is being returned to its start position by PZA 168. When rotation direction is to be reversed, PZA 168 becomes the power PZA, and PZA 170 the return.

Figure 10A:
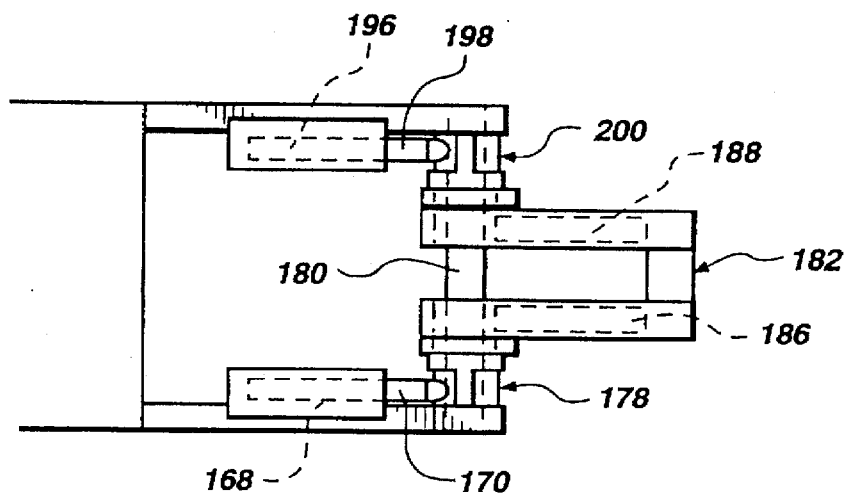
FIG. 10A is a top view of a modification of the alternative embodiment of the finger motor of FIGS. 9 and 10.

The embodiment of FIGS. 9 and 10 may be further modified by employing a second set of drive PZA's 196 and 198 to drive a second rotator 200, as showing in FIG. 10A. By employing such an arrangement, distal segment 182 could be continuously driven, as rotator 178 could drive segment 182 while rotator 200 is being reset to its start position, thus substantially doubling potential rotation speed while maintaining applicable torque.

In the example illustrated in connection with FIG. 6, prior to time t1, PZA 90A was already in the elongated state and PZA 90B was in the shortened state. Under a first computer program (followed in the FIG. 6 example), PZA 90B would remain in the shortened state unless it was necessary for it to be elongated. Under a second computer program, both PZA 90A and PZA 90B would be elongated prior to the beginning of a rotation sequence.

In the first preferred embodiment, in response to being energized, the PZA's are elongated and shortened in the direction of arrows 70 in FIG. 2A. However, as previously noted, bending type field actuators are known and may be suitable for some applications of the present invention where greater displacements (and thus motor speed) are desirable, and force (and thus motor torque) is less critical.

The first preferred embodiment could be modified if desired so that section 14 includes one oscillating drive structure and one clamping structure and section 16 could include one oscillating drive structure and one clamping structure, instead of the arrangement of the preferred embodiment, where both drive structures are carried by segment 14 and both clamping structures by segment 16.

It is also contemplated that a "half" finger motor 10 as depicted in FIGS. 1 through 4 of the drawings may be fabricated using only a single drive structure 32A and a single clamping structure 78A. Such an embodiment would operate like a water wheel or impulse wheel, with PZA 44A drive strokes and clamping of segment 16 to bushing 26A by PZA 90A being appropriately timed. While such an embodiment would lack the power of the preferred embodiment, it would be suitable for many applications.

Figure 27:
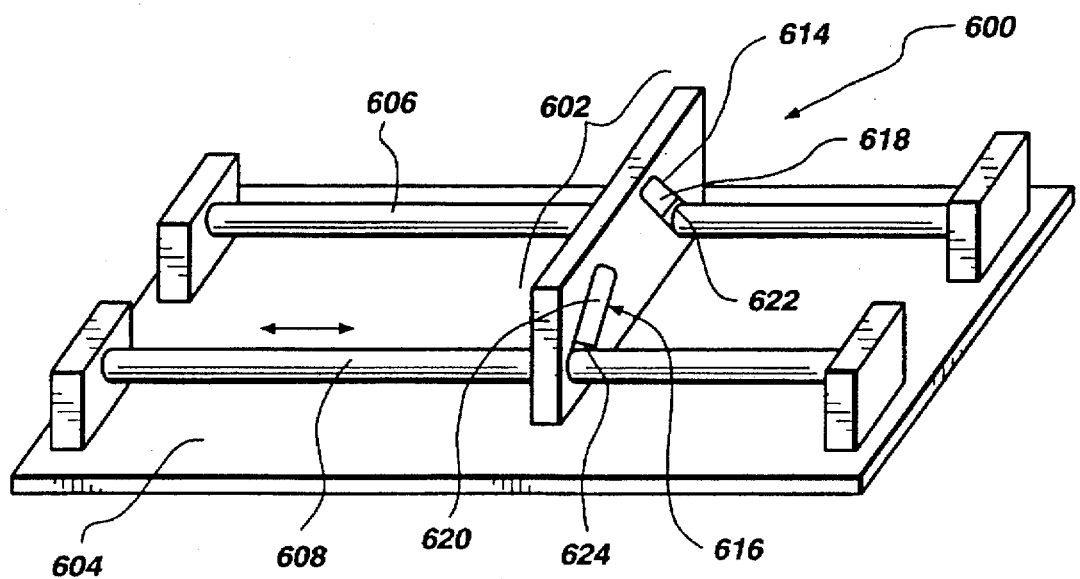
FIG. 27 is a schematic perspective of a linear finger motor.
Figure 28:
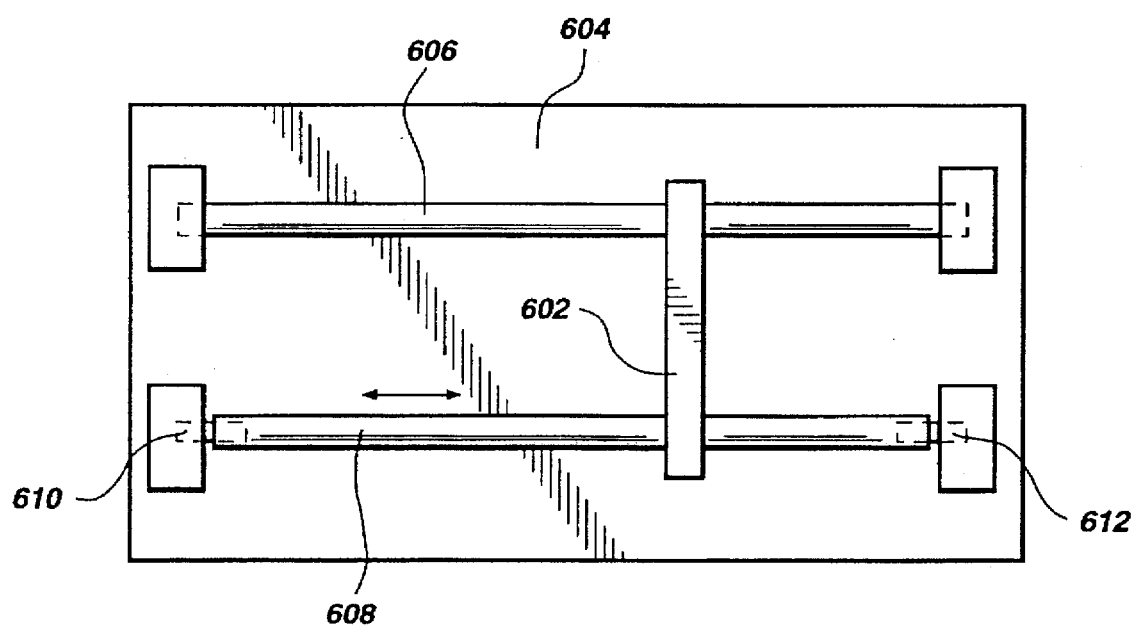
FIG. 28 is a top elevation of the linear finger motor of FIG. 27.

Yet another alternative embodiment of the finger motor is a linear motor, illustrated in FIGS. 27 and 28. In this embodiment, motor 600 provides linear translational movement of an element 602 relative to a supporting base 604. Base 604 has supported thereon a fixed cylindrical guide shaft 606 and a longitudinally oscillating or reciprocating drive shaft 608 extending parallel to guide shaft 606. PZA's 610 and 612 are positioned at respective ends of drive shaft 608, and are interposed between the shaft ends and supports secured to the base 604. Movable element 602 may comprise a plate having two clamping structures 614 and 616 driven by PZA's 618 and 620 acting on clamping shoes 622 and 624, clamping structure 614 having the ability to selectively lock element 602 to guide shaft 606 and clamping structure 616 having the ability to selectively lock element 602 to drive shaft 608.

Element 602 is moved by clamping same via clamping structure 616 to oscillating drive shaft 608 prior to the time the later move longitudinally in the desired direction responsive to the timed energizing and de-energizing of PZA's 610 and 612, and releasing element 602 from drive shaft 608 at the end of its stroke in that direction substantially simultaneously and clamping element 602 to fixed guide shaft 606 via clamping structure 616 to prevent backward movement of element 602 as drive shaft 608 resets for another power stroke. Thus it is readily apparent that motor 600 operates in exactly the same manner as finger motor 10, only in a linear mode.

It will also be apparent that two or more oscillating parallel drive shafts 608 may be employed and that guide shaft 606 may in some instances be eliminated. With two drive shafts, power or drive strokes can be more frequently applied to element 602, increasing the potential speed thereof. Furthermore, it is contemplated that only a single PZA be employed per drive shaft, and a spring or other resilient member be placed at the opposite end to effect a "return" stroke of the shaft. Finally, two elements 602 may be employed in motor 600, and used as movable gripping jaws by appropriately timed locking and unlocking to one or more drive shafts 608 to move each element 602 in the desired direction.

Further with respect to finger motor embodiments, it is also contemplated that a finger motor having a segment 16 capable of continuous rotation rather than limited rotation through less than a 360° arc may be easily fabricated by using slip ring commutators to transmit electrical power to the clamping structure or structures (or drive structures) carried by the rotating segment.

B. Star Motor

The following text describes several embodiments of linear star motors and rotary star motors. Star motors are believed to have particular utility when employed in combination with rotating joints for robotic limbs, for extensible limbs, and for robotic hands having powerful grips. Such motors can possess a holding torque of about four times stall torque, and have a high positioning accuracy as small-increment stepper motors. They can be designed to be either serf-braking or free-wheeling when power is lost, and in certain applications can be made highly redundant with only a small weight gain, so that if a particular drive set of a motor becomes inoperative, the motor is still able to function. The motors are very robust and very compact, being substantially two-dimensional with a very thin third dimension. Multiple stator assemblies may be stacked to even further enhance the torque applied to a common rotor without losing the compact character of the motor. Finally, the star motor is equally adaptable to rotary and to linear motion.

1. Linear Star Motor

Figure 11:
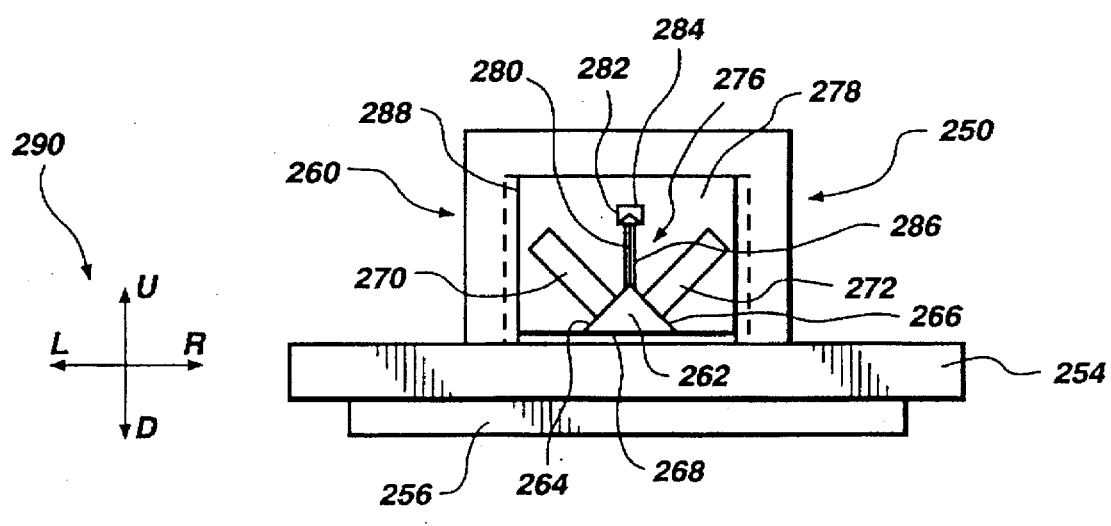
FIG. 11 is a side view of a first preferred embodiment of a V-drive linear star motor.

FIG. 11 shows a side view of a first preferred embodiment of a V-drive linear star motor 250. An element 254 to be driven, such as a metal rod, plate or strip, is supported by a support 256. A drive mechanism 260 includes a substantially triangular drive shoe 262, a PZA 270, a PZA 272, and a biasing structure 276, all assembled in a stator block 278, preferably a solid piece of metal. Drive shoe 262 includes upper surfaces 264 and 266 adjacent PZA's 270 and 272, respectively, and lower drive surface 268 which lies over element 254. PZA's 270 and 272 are each oriented at an oblique angle to element 254, defining a "V" shape. The included angle of the "V" should optimally be between 45° and 135°. The angle may vary depending upon whether motor speed or force is to be optimized, or a compromise achieved. For example, using a "narrow" V-drive with a small included angle and both PZA 270 and 272 oriented more perpendicularly with respect to element 254 will result in relatively higher forces being applied to element 254 through drive shoe 262 than if PZA 270 and 272 were oriented in a "wide" V, the latter configuration providing more displacement of element 254 per cycle of drive shoe 262, but at the expense of force.

Biasing structure 276 may include a Belleville washer 282 and music wire 280 attached to drive shoe 262, the former disposed in washer cavity 284 and the latter extending to show 262 through a slot or channel 286 in stator block 278, to pull drive shoe away from contact with element 254. Upward biasing of drive shoe 262 may, of course, be provided by other arrangements, but the configuration disclosed is particularly simple and effective. When either of PZA 270 or PZA 272 is energized, it presses against drive shoe 264, which in turn presses against element 254. When neither PZA 270 nor PZA 272 is energized, biasing structure 276 pulls drive shoe 262 slightly away from element 254. Schematically depicted slide mechanism 288 may adjust the position of drive mechanism 260 up and down to accommodate elements 254 having widely differing thicknesses. Slide mechanism 288 may comprise a simple, set screw lockable against ridges on stator block 278 received in channels in support structure 292, or may comprise a precise gear-type adjustment with micrometer settings, or even comprise another star motor drive unit acting on stator block 278 in a direction perpendicular to element 254. If the only adjustment required is to accommodate dimensional tolerances of similar elements 254, a simply adjustment set screw threaded into stator block 278 and being on the upper ends of PZA 270 and 272 and longitudinally aligned therewith may be employed for this purpose, as such may be included in any case in motor 250 to assist in the proper loading of drive shoe 262 by PZA's 270 and 272.

Figures 12, 12A:
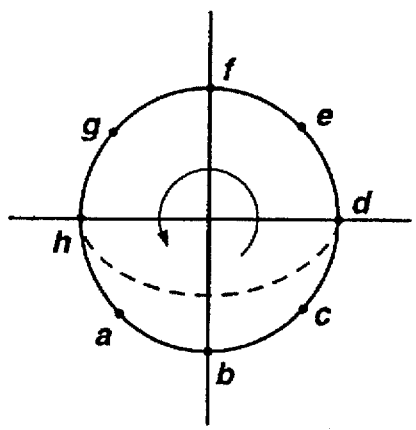
FIG. 12 is a graphic illustration of the actuator operating sequence of the V-drive linear star motor of FIG. 11.
FIG. 12A is a graphic illustration of the drive show positions of the star motor of FIG. 11, corresponding to the actuator operating sequence depicted in FIG. 12.
Figure 17:
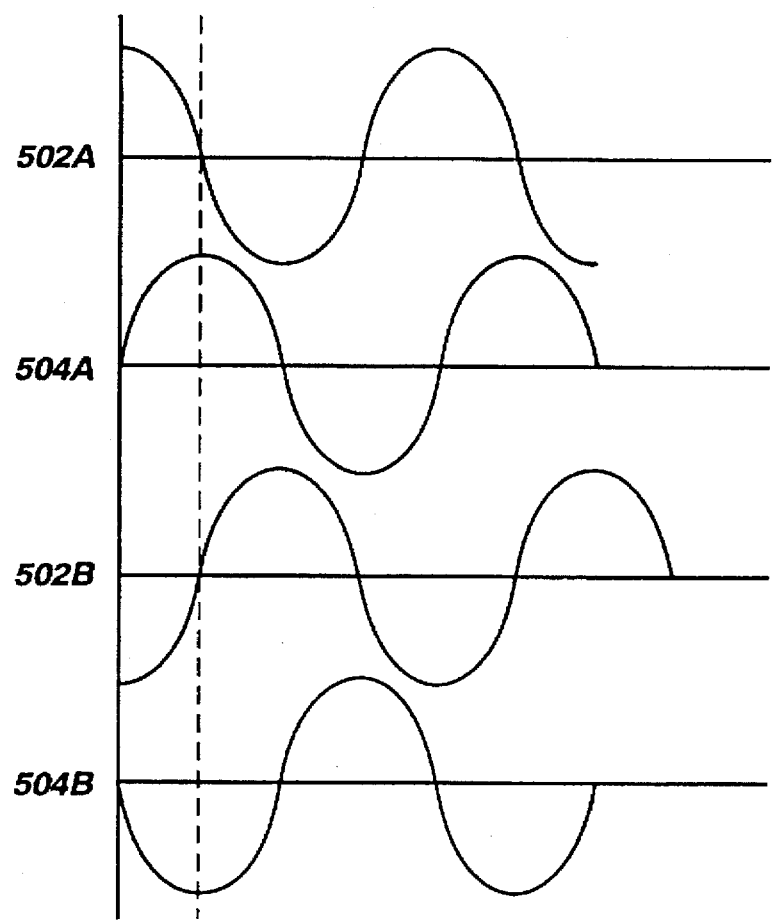
FIG. 17 depicts the phased sine wave signals employed in a two-phase drive for the star motor of FIGS. 15 and 16.

FIGS. 12 and 12A graphically depict the operation of V-drive linear star motor 250, FIG. 12 depicting the energization states of PZA 270 and PZA 272 as driven by phased sine waves as depicted in FIG. 17. "E" indicated a PZA is energized, and "NE" that it is not energized. Fractions next to an "E" indication set forth the approximate degree of energization due to the sine wave drive signal. FIG. 12 also depicts the direction of movement of drive shoe 262 and of element 254 corresponding to the energization states of PZA's 270 and 272, the directions being keyed into those indicated in FIG. 11. "NM" indicates no movement of an object. FIG. 12A depicts the generally circular nature of the trajectory of drive shoe 262, and letters a through h indicate different positions of drive shoe 262 which, by like letters at the top of FIG. 12, are shown to correspond to the different energization states of PZA's 270 and 272 for times $t_0$ through $t_8$. The broken line in FIG. 12A depicts a flattened, more ellipsoidal trajectory resulting from contact of drive shoe 262 with element 254. It should be noted that the biasing structure associated with motor 250 causes some movement of the drive shoe 262, and that effect has been accounted for in FIGS. 12 and 12A. Moreover, it should be noted that the phase relationship between the motor drive signals can be modified to create a more ellipsoidal drive shoe trajectory, with the long axis of the ellipse oriented as desired. It should also be noted that the angles of drive shoe faces 265 and 266 as well as the included angle between PZA's 270 and 272 will also affect the trajectory of drive shoe 262.

Figure 13:
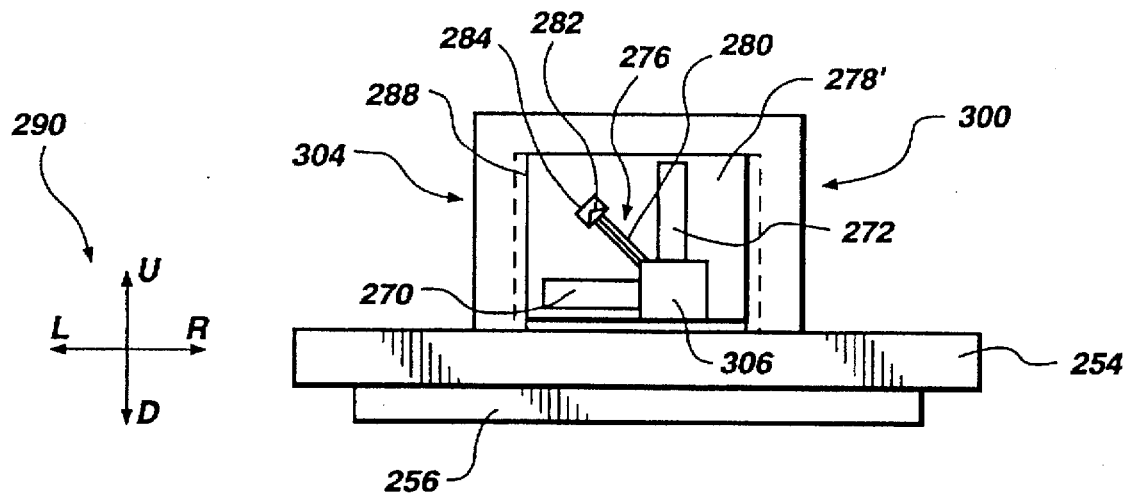
FIG. 13 is a side view of a first preferred embodiment of an L-drive linear star motor.

FIG. 13 shows a side view of a first preferred embodiment of an L-drive linear star motor 300. Elements of motor 300 which are the same as those of motor 260 are numbered the same. Driven element 254 is again supported by a support 256. A drive mechanism 304 includes a drive shoe 306, a PZA 270, a PZA 272, and a biasing a biasing structure 276, all assembled in a stator block 278. Drive shoe 306 is preferably rectangular or square shaped. PZA 270 is oriented parallel to the orientation of driven element 254, while PZA 272 is oriented perpendicular thereto. In the L-drive motor, when PZA 270 is energized it moves drive shoe 306 to the right. When PZA 272 is energized, it moves drive shoe 306 down until it firmly presses against element 254. When neither PZA 270 nor PZA 272 is energized, biasing structure 276 pulls drive shoe 306 slightly away from element 254. Thus, a substantially triangular drive shoe trajectory is provided. A slide mechanism 288 permits adjustment of drive mechanism 304 up and down to accommodate driven elements of significantly different thicknesses.

Figure 14:
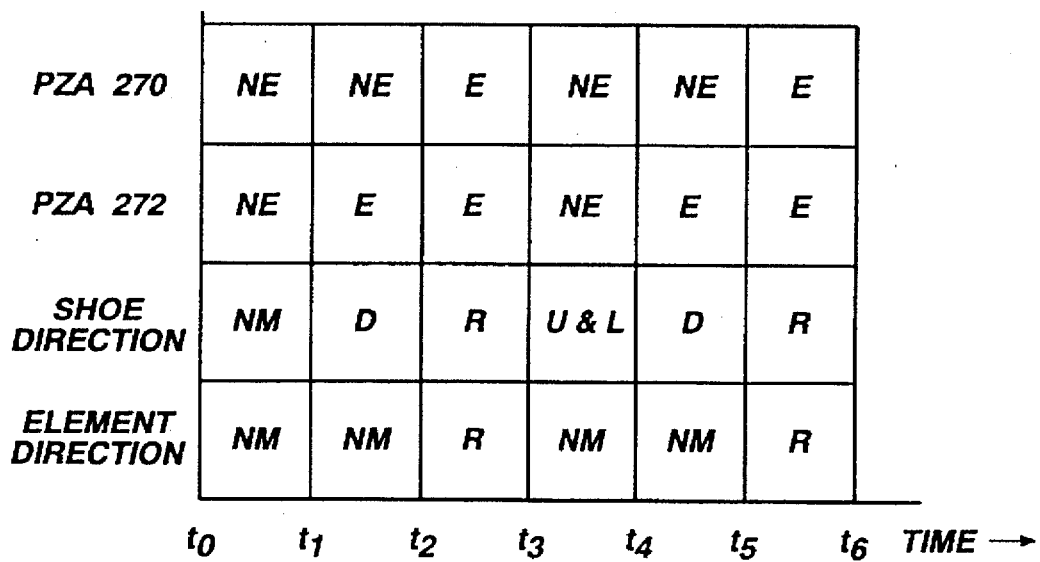
FIG. 14 is a graphic illustration of the actuator operating sequence of the L-drive linear star motor of FIG. 13.

FIG. 14 graphically illustrates the operation of L-drive linear star motor 300. FIG. 14 uses the same symbols as were used in FIG. 12 with respect to energization of the PZA's, the movement directions of drive shoe 262 and element 254 are keyed to FIG. 13, and "NM" indicates no movement of an object. From time to $t_0$ to time $t_1$, both PZA 270 and PZA 272 are de-energized and drive shoe 306 does not engage element 254 with any significant force. From time $t_1$ to time $t_2$, PZA 270 is de-energized and PZA 272 is energized moving shoe 306 downward until it firmly engages object 254. From time $t_2$ to time $t_3$, PZA's 270 and 272 are energized, the former moving drive shoe 306 to the right, which in turn moves element 254 to the right. From time $t_3$ to time $t_4$, PZA's 270 and 272 are de-energized and biasing structure 276 returns drive shoe 306 upward and to the left to its original position. From time $t_4$ to time $t_5$, PZA 270 is de-energized and PZA 272 is energized moving shoe 306 downward until it again firmly engages element 254. From time $t_5$ to time $t_6$, PZA's 270 and 272 are energized moving drive shoe 306 to the right, which in turn moves element 254 to the right. The durations between times are not necessary equal. For example, the time between times $t_2$ and $t_3$ is not necessary the same as the time between times $t_3$ and $t_4$. If it is desired to reverse the direction of motor 300, the energizing sequence of PZA's 270 and 272 is altered so that element 254 is contacted by shoe 306 as it is retracted to the left by biasing structure 276.

2. Rotary Star Motor

Figure 15:
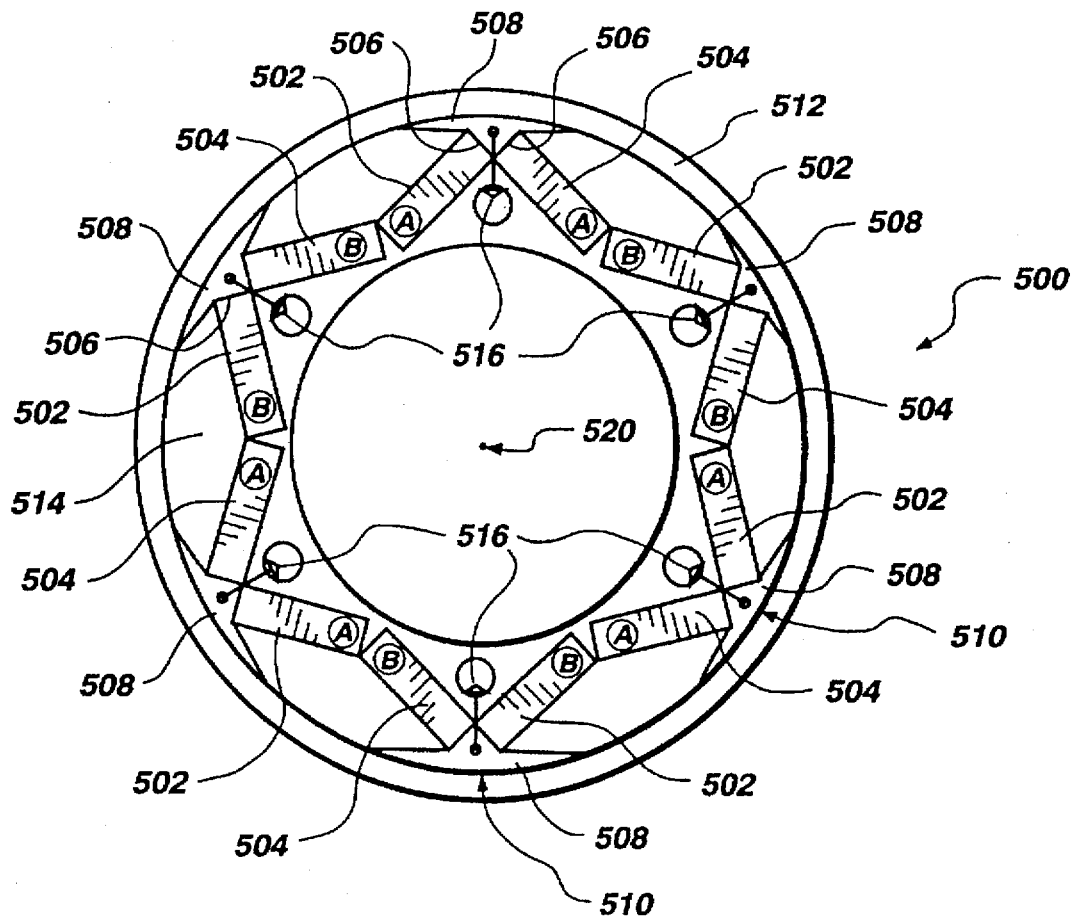
FIG. 15 is a side or plan elevation of a rotary star motor employing a V-drive.

Referring to FIG. 15 of the drawings, a V-drive rotary star motor 500 is illustrated with the rotor disk, shaft and bearing assembly omitted for clarity. Motor 500 includes multiple drive assemblies comprising pairs of PZA's 502 and 504 oriented at a mutual included angle of substantially 90°, the drive faces of PZA's 502 and 504 each abutting load faces 506 of drive shoes 508, the outer arcuate surfaces 510 of which engage the I.D. of rotor 512 disposed about stator assembly 514, which carries the drive assemblies. As with the previously described linear star motors, rotary star motor 500 biases each drive shoe 508 in tension by suitable biasing structures 516. The energization sequence for the paired PZA's is the same as previously described with respect to the linear V-drive star motor, and as illustrated in FIG. 12 of the drawings.

Figure 16:
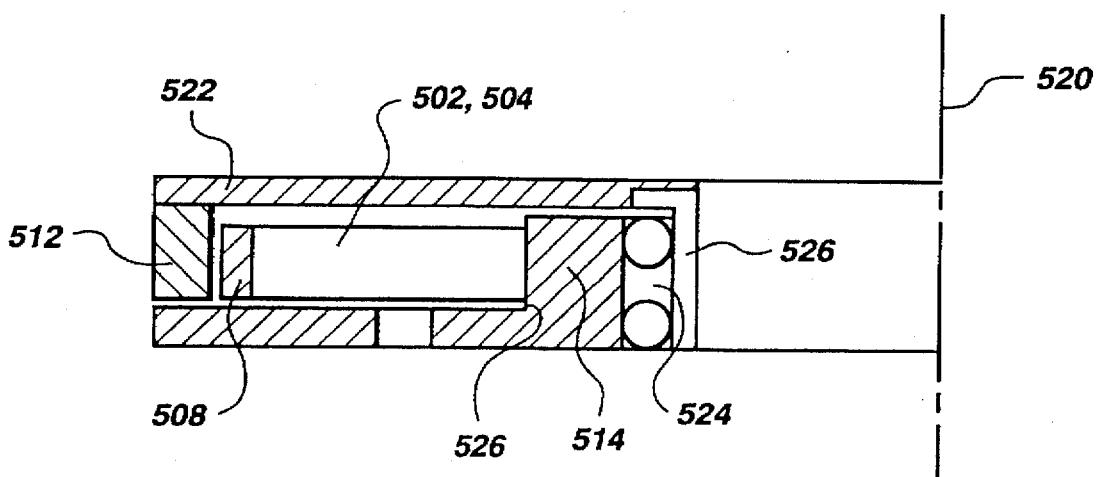
FIG. 16 is a partial side sectional elevation of the rotary star motor of FIG. 15.

FIG. 16 depicts a side sectional elevation of motor 500 of FIG. 15, taken from the center line 520 of motor 500 and showing the rotor disk 522 overlying and secured to the rotor rim 512 and bearing 524 by which rotor shaft 526 and thus the entire rotor is free to rotate with respect to stator assembly 514. FIG. 16 also shows a layer of Teflon® (tetrafluoroethylene) sheeting or other friction-reducing material 526 under PZA 502, 504, which layer reduces friction between the rapidly expanding and contracting PZA's and stator assembly 514. It is also desirable that the sides of the cavities in stator assembly 514 which receive PZA's 502 and 504 also be lined with Teflon® or other friction-reducing material to facilitate expansion and contraction of the PZA's and lessen wear and friction-induced heating of the motor.

All of the pairs of PZA's may be driven in single phase, but it is preferred to operate alternate pairs of PZA's out of phase so as to achieve smoother movement of rotor 512 and lower noise levels. It is further contemplated that more phases be employed. For example, in a six-drive assembly motor as depicted in FIG. 15, each of the drive assemblies may be drive in different phases to provide smooth torque output, in contrast to operating all six drive assemblies in phase, which would provide a great deal of force but a substantial torque ripple from the motor. This ability to change motor output characteristics of a multiple drive assembly motor by varying the drive signal phasing provides significant flexibility to address a variety of operating requirements. As with the shoes of the linear V-drive star motor, shoes 508 of motor 500 translate in a circular or ellipsoidal path, and reversal of rotor direction or rotation is achieved by simply reversing the PZA energization sequence.

FIG. 17 of the drawings depicts the sinusoidal voltage waveform timing preferably employed for rotary star motor 500 for two-phase activation of the PZA's, the paired PZA's being identical as either "A" phase or "B" phase in both FIGS. 15 and 17.

It is, of course, possible to fabricate an L-drive rotary star motor, the details of which will be apparent from the previous description of the linear L-drive motor. The L-drive may possess several advantages over the V-drive in a rotary star motor configuration, including compactness, so that more actuator pairs may be employed for a given motor diameter. In addition the L-drive tangential PZA may be smaller than the PZA's employed in the V-drive embodiment as the former is aligned with the direction of rotor element movement and thus needs only to produce a force equal to the radially applied force of the normal PZA times the coefficient of friction between the drive shoe 510 and the normal PZA, in contrast to the V-drive embodiment wherein each PZA produces a radially and tangentially applied force and there is frictional sliding contact between the inner drive shoe surfaces and both PZA's.

As with the other embodiments of the present invention, the rotary (and linear) star motors may be fabricated without the use of exotic materials and at a reasonable cost. The stator assembly body may be aluminum machined into a disk and having channels milled therein to accept PZA's. As noted above, the PZA channels are lined with Teflon strips, and a thin aluminum retention plate, also having appropriately placed Teflon straps adjacent PZA's, is secured over the stator with screws. The drive shoes may be aluminum, anodized aluminum, steel, tungsten carbide, aluminum bronze, ceramics or other wear-resistant materials known in the art. The biasing structure may comprise music wire tensioned by one or more Belleville washers or other spring means. The rotor shaft may be steel, as may the rim, both being secured to an aluminum rotor disk. Alternatively, the rotor rim, disk and shaft may comprise a single piece.

3. Alternative Configurations and Applications of Star Motors

Figure 18:
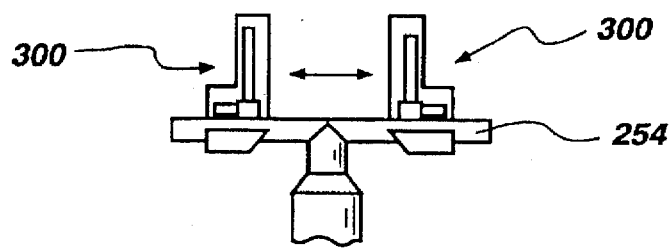
FIG. 18 is a schematic side elevation of two L-drive star motors configured as a robotic gripper.
Figure 18A:
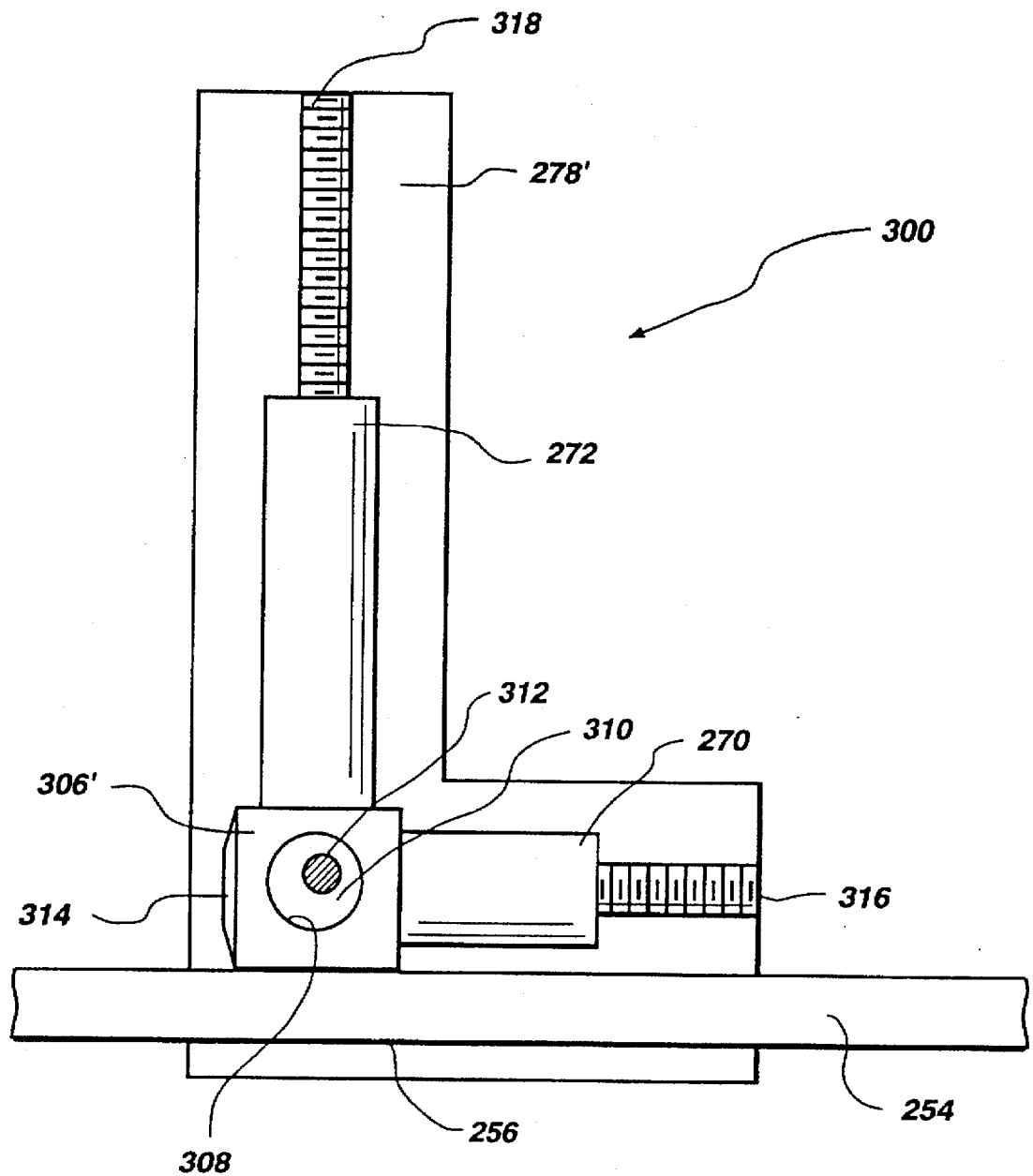
FIG. 18A is an enlarged side elevation of the right-hand star motor depicted in FIG. 18.
Figure 19:
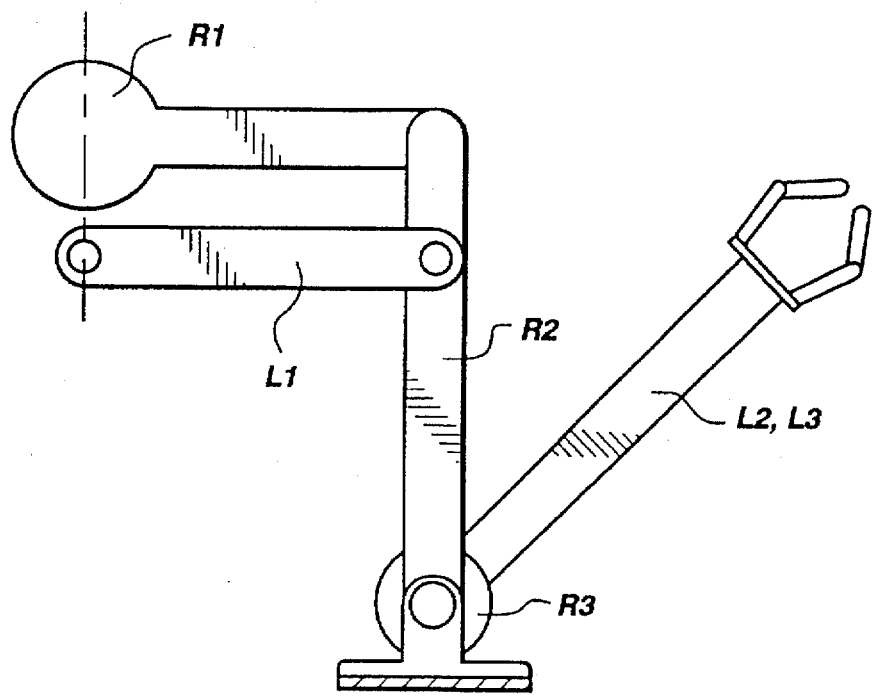
FIG. 19 is a schematic side elevation of a prehensile robotic leg employing multiple star motors.

It will be readily appreciated by those of ordinary skill in the art that the star motors admit to a variety of diverse applications. For example, as shown in FIG. 18, two L-drive motors 300 may be mounted on a straight bar and each function as a jaw of a robotic gripper. L-drive motors are preferred for their aforementioned compactness, although a V-drive gripper could also be fabricated. FIG. 18A is an enlarged view of right-hand L-drive motor 300.

L-drive motor 300 of FIG. 18A includes PZA's 270 and 272 carried in a stator block 278' and acting on a modified rectangular drive shoe 306' which moves stator block 278' on bar 254. Drive shoe 306' includes an aperture 308 therethrough having a resilient element 310 set therein, and a screw, bolt or rod 312 extending through resilient element 310 and secured to stator block 278 (securing means not shown) to pre-load resilient element 310 and provide a bias upwardly and to the right for drive shoe 306'. Disk spring 314 may also be employed to bias drive shoe 306'. Adjustment set screws 316 and 318, previously referenced with respect to other embodiments of the star motor, are shown in FIG. 18A. Support 256 may include on its upper surface a friction-reducing coating to facilitate movement of stator block 278' on bar 254. FIG. 18A is thus illustrative of other and further variations of the L-drive motor of the present invention.

As noted above, multiple stators may be employed with a single rotor in the rotary star motor, to multiply torque. The stators may be joined or separate, and drive separate or a common rotor. The rotors may be driven on their O.D.'s if desired, with the PZA's and drive shoes facing readily inward or rotors may be driven on both their I.D.'s and O.D.'s. Rotors may also comprise disks rather than rings, and the PZA drive assemblies may be oriented at an angle to the disk plane and act upon the rotor disk surface. Seals may be employed between the rotor rim and the stator to prevent particulate intrusion. Various types of bearing may be employed, and a solid lubricant such as molybdenum disulfide is preferred.

Figure 20:
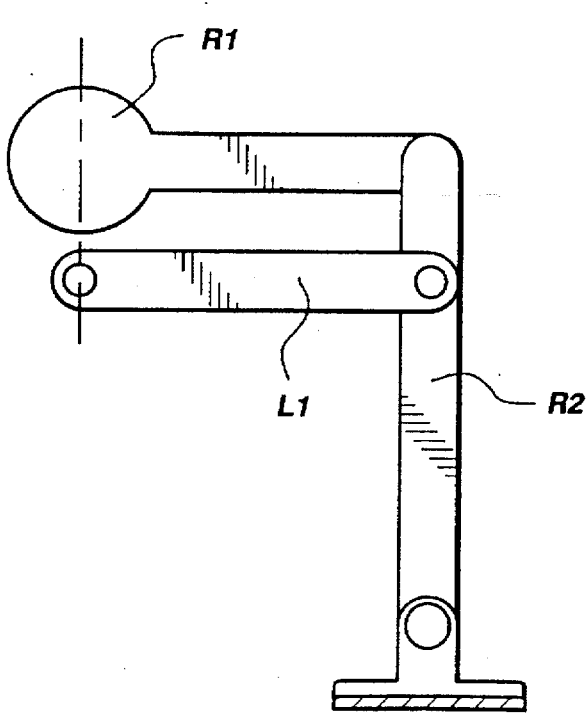
FIG. 20 is a schematic side elevation of a normal robotic leg employing multiple star motors.
Figure 21:
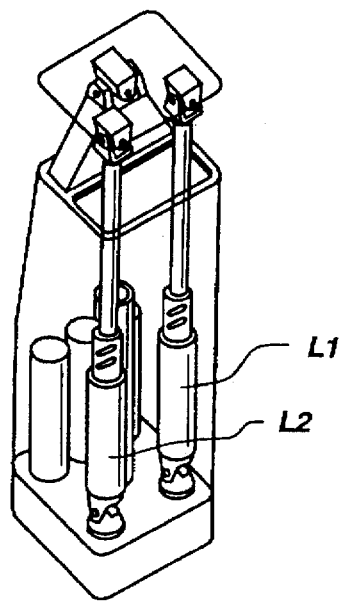
FIG. 21 is a schematic perspective view, partially in phantom, of a robotic wrist employing linear star motors for pitch and yaw control.
Figure 22:
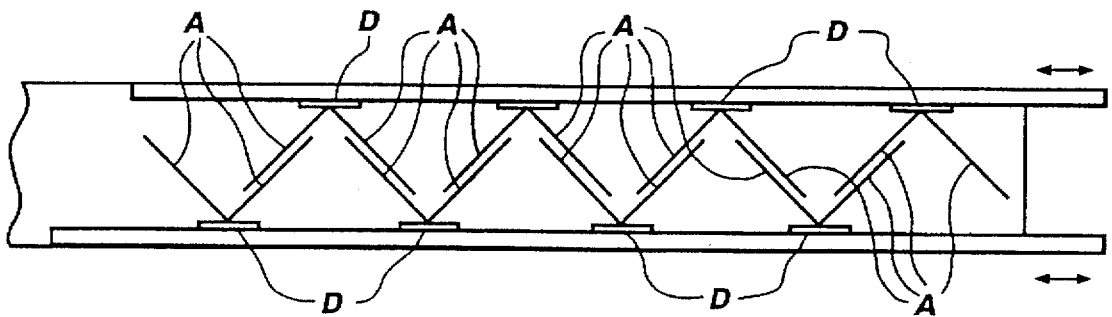
FIG. 22 is a schematic side elevation of a compact tandem linear star motor arrangement having utility in the robotic wrist of FIG. 21.
Figure 23:
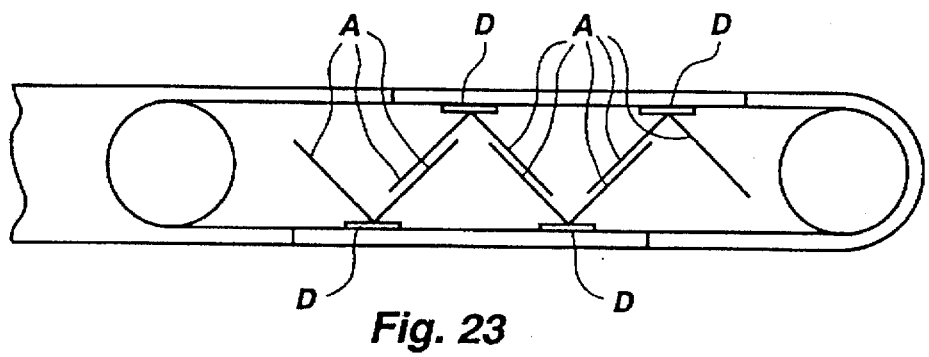
FIG. 23 is a schematic side elevation of a compact tandem linear star motor arrangement for robotics foot rotation.
Figure 24:
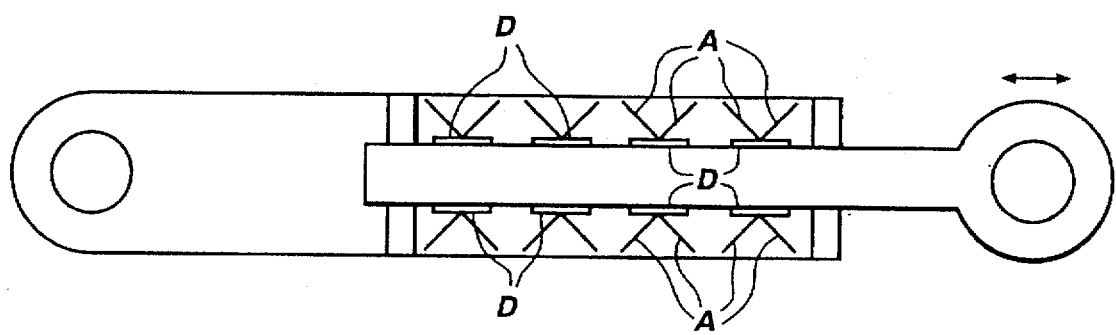
FIG. 24 is a schematic side elevation of a high power tandem star motor in an "X" drive configuration, for driving an extensible robotic thigh.

FIGS. 19–24 schematically depict various robotics applications for rotary and linear star motors employing actuators A and drive shoes D. The device of FIG. 19 employs three rotary motors R1–R3 and three linear motors L1–L3 in a prehensile leg, which may also employ finger motors in the "hand" at the end of the forearm. FIG. 20 depicts a normal leg using a two rotary motors R1–R2 and a single linear motor L1. If desired, a small rotary star motor may be employed in the robot "ankles" of FIG. 19 to provide the forearm with the ability to rotate at its base about a vertical axis. FIG. 21 depicts a robotic wrist design employing two linear star motors L1 and L2 for wrist pitch and yaw control. FIG. 22 depicts staggered parallel, overlapping outwardly facing rows of linear star motors, which may be used in configurations requiring compactness for the pitch and yaw control in the robotic wrist of FIG. 21. FIG. 23 depicts a staggered, parallel, overlapping outward facing rows of linear star motors employed as a robotic foot rotation motor, for example as motor R2 in FIGS. 19 and 20. It should be noted in FIG. 23 that the rotor element may comprise a flexible strip or band. FIG. 24 depicts an "X" drive star motor, with parallel, inwardly facing rows of linear star motors used to extend and retract a robotic thigh. Of course, many other combinations of rotary and linear star motors are possible, and many also are used in combination with the previously-described finger motors and the subsequently-described ratchet motors.

Figure 29:
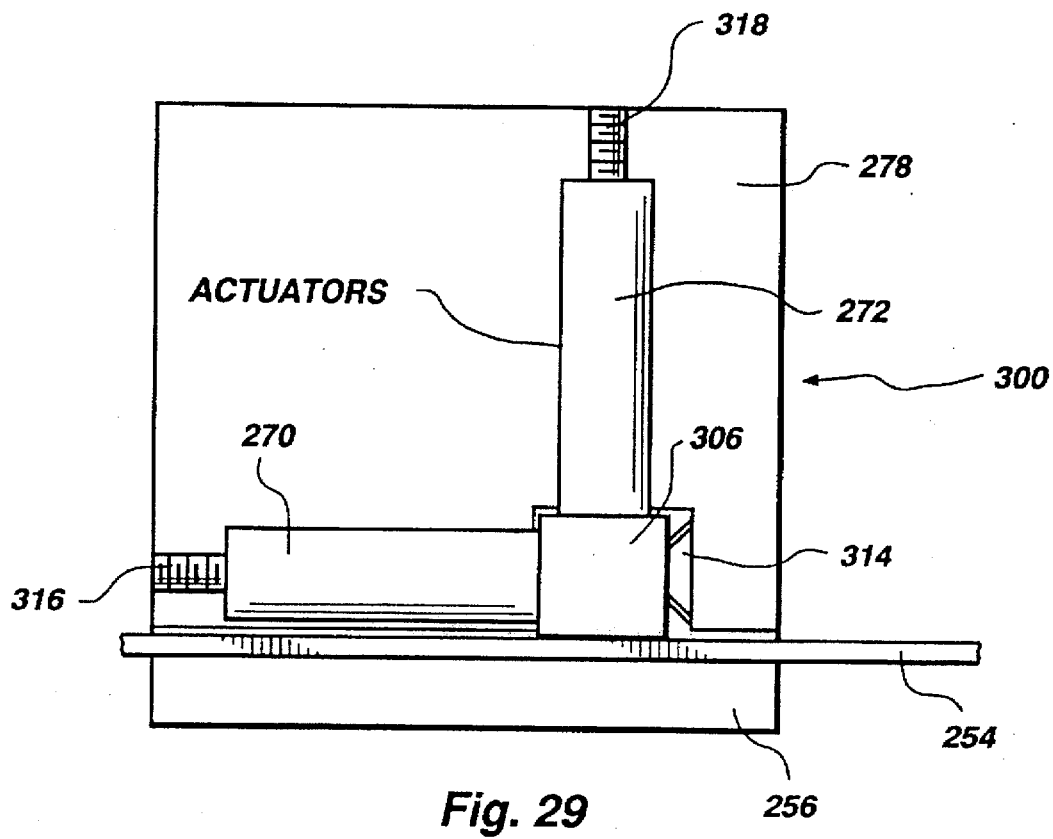
FIG. 29 is a side elevation of an alternative L-drive linear star motor configuration.

FIG. 29 depicts a modified L-drive linear star motor 300 employing only a disc-type shoe return spring 314 in lieu of the biasing arrangements previously described.

Figure 30:
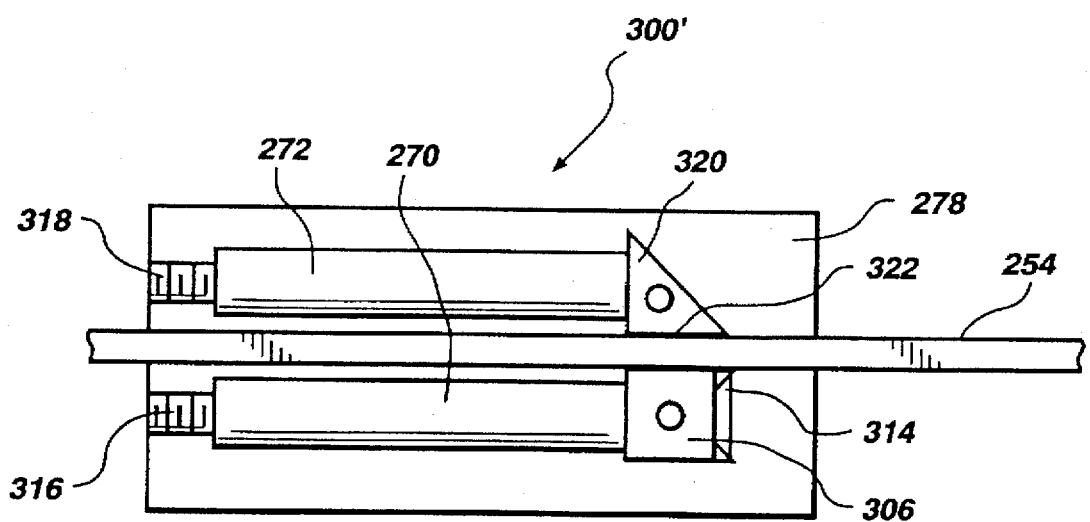
FIG. 30 is a side elevation of a parallel-drive alternative linear star motor according to the present invention.

FIG. 30 depicts a parallel-drive linear star motor 300' wherein normally perpendicular PZA 272 is oriented parallel to element 254 to conserve space. PZA 270 is disposed under element 254 and a clamping effect to ensure firm contact of drive shoe 306 with element 254 is achieved with clamping wedge 320. In this embodiment it is desirable to coat or cover the element-contacting face of clamping wedge 320 with a friction-reducing material 322.

Figure 31:
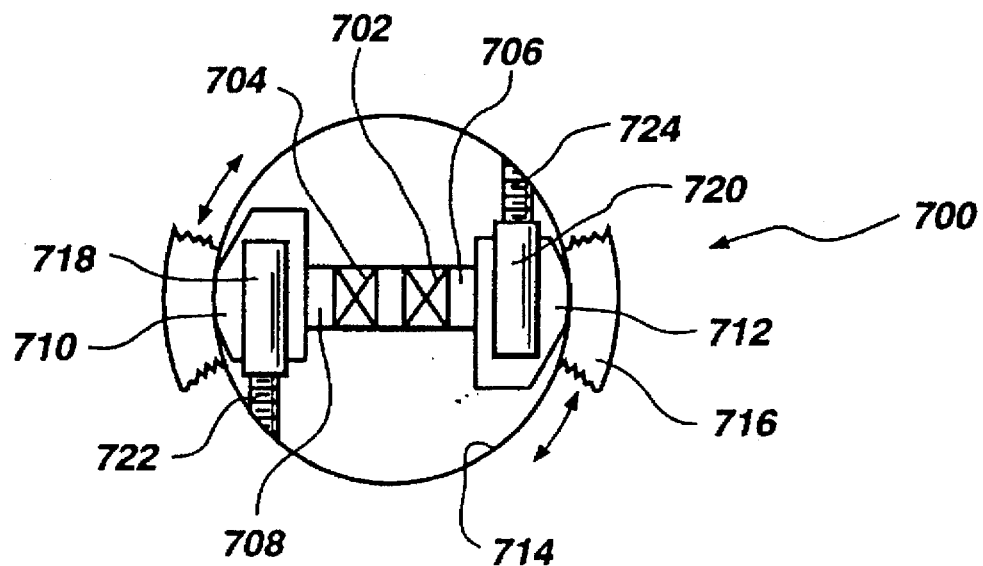
FIG. 31 is a top schematic elevation of a modified, compact L-drive rotary star motor according to the present invention.
Figure 32:
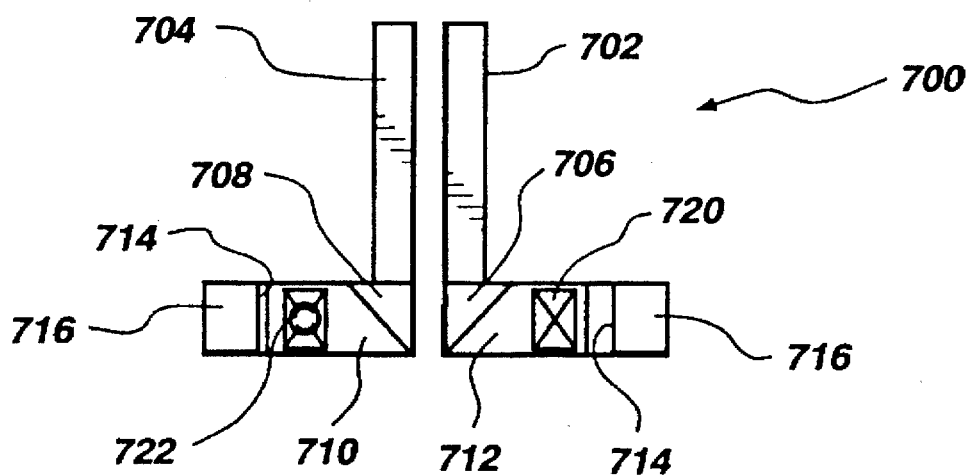
FIG. 32 is a side schematic elevation of the motor of FIG. 31.

FIGS. 31 and 32 depict yet another modification of an L-drive star motor which in some respects is similar to the motor of FIG. 30 and in some respects similar to the previously-described finger motor in that the motor of FIGS. 31 and 32 employs a clamping structure. Motor 700 includes clamping PZA's 702 and 704 which act on clamping wedges 706 and 708 to move drive shoes 710 and 712 outwardly against the inner rim 714 of a rotor structure 716 at appropriately timed intervals as drive PZA's 718 and 720 are periodically energized to move drive shoes 710 and 712 substantially tangentially to inner rim 714 and thus cause rotor structure 716 to rotate. Adjustment set screws (such as 722, 724 shown) are employed to ensure firm contact of the PZA's with the elements they act upon. If desired, resilient return members may be added at appropriate locations to motor 700 to reset drive shoes 710 and 712 when PZA's 718 and 720 are de-energized, and to reset clamping wedges when PZA's 702 and 704 are de-energized. It may further be desirable to add a friction-reducing material between the clamping wedges and the drive shoes, and around the PZA's, to facilitate expansion and contraction thereof.

While the star motors described above have been single-degree of freedom motors wherein rotor elements move in a single linear or arcuate path, the invention is not so limited. Motors wherein a rotor element rod is moved linearly and also rotated about its axis by an appropriately shaped drive shoe are clearly possible, and contemplated as within the scope of the invention. Similarly, a sheet or plate-type rotor element may be moved in any direction in its plane by appropriate orientation of several PZA-drive assemblies, such as one at an "X" direction and one in a "Y" direction at 90° to the "X" direction, movements in other directions in the plane being achievable by combined actuation of the two (or more) dissimilarly oriented drive assemblies.

C. Ratchet Motor

Figure 25:
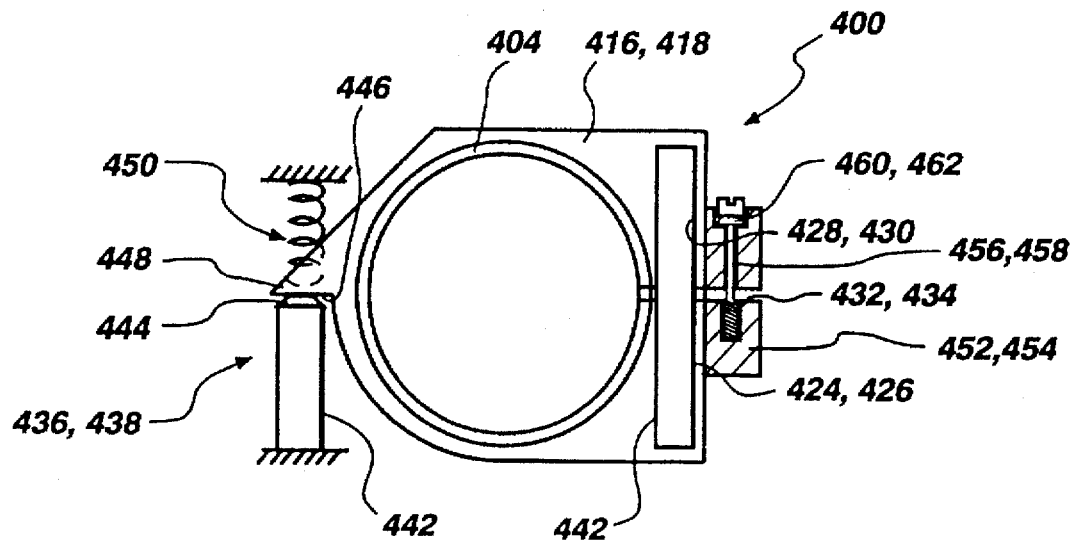
FIG. 25 is a schematic side elevation of a preferred ratchet motor embodiment of the present invention.
Figure 26:
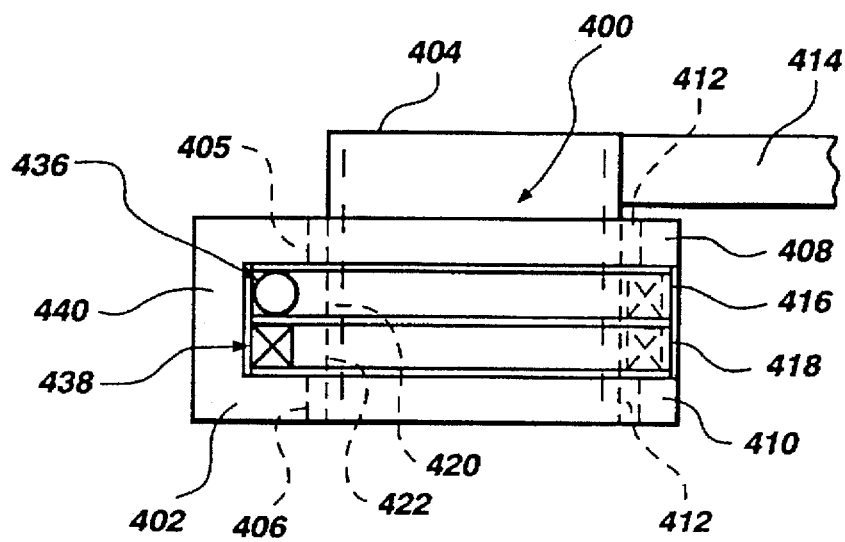
FIG. 26 is a schematic top elevation of a preferred ratchet motor embodiment of the present invention.

Referring now to FIGS. 25 and 26 of the drawings, a ratchet motor 400 according to the present invention is schematically depicted inside elevation and top elevation, respectively. Ratchet motor 400 comprises a stator assembly 402 supporting a rotor 404, which extends through aligned bushing cavity 405, 406 in the two legs 408, 410 of stator assembly 402. Rotor 404 is supported in each bushing cavity 405, 406 by circular bushings 412 so that it may freely rotate and resist cocking or jamming under uneven or offset application of loads, such as might be experienced if ratchet motor is employed to rotate the "wrist" or "thigh" of a robotic limb to the side, in a motion which may be termed "yaw". In such a robot, stator assembly 402 would preferably be secured to or be part of the robot torso, and rotor 404 secured to an arm or leg element or limb 414 of the robot.

Two split-ring clamping assemblies 416, 418 having clamping apertures 420, 422 therethrough are disposed within the legs 408, 410 of stator assembly 402 and about rotor 404. The inner diameter (I.D.) of clamping apertures 420, 422 is less than the outer diameter (O.D.) of rotor 404 when clamping assemblies 416, 418 are in a relaxed, unstressed state. PZA's 424 and PZA 426 are disposed in cavities 428 and 430, respectively, in clamping structures offset from and in substantially tangential orientation to rotor 404, bridging slits 432, 434 in clamping assemblies 416, 418. When PZA 424 or 426 is energized, it expands its respective clamping assembly to permit relative rotation of rotor 404. When the PZA is de-energized, the clamping assembly locks onto rotor 404 due to the elastic nature of the clamping assembly material. The split-ring clamping assemblies may be analogized to the oscillating clamping structures of the finger motor embodiment.

Stator assembly 402 houses at least one, but preferably two, oscillating drive assemblies 436, 438 proximate the base 440 of the assembly. Drive assemblies 436, 438 each comprise a PZA 442 having a drive shoe 444 which bears against radially aligned (with respect to rotor 404) outwardly extending drive surface 446 of drive tab 448 on a clamping assembly 416 or 418 (see FIG. 25). Opposing and longitudinally aligned with PZA 442 is resilient return member 450, which may comprise a coil spring, elastomeric element, one or more Belleville springs, or one or more leaf springs, as desired. If it is desired to effectuate rapid, substantially continuous motion of rotor 404, two drive assemblies may be employed, either oriented in the same manner or in opposing orientations (with one of the clamping assemblies reversed) so as to provide a positive drive via a PZA in each direction of rotation. A single PZA may, of course, be employed, and the stored energy of component return member 450 be employed to rotate rotor 404 as described with respect to the finger motor. It is also contemplated that three, four or more drive assemblies may be "stacked" as with the star motor drives, and driven in multiple phases if desired for a smoother torque output and/or higher speeds.

In addition to the inherent resiliency of split-ring clamping assemblies 416, 418, the assemblies 416, 418 may also optionally include protrusions 452, 454 (see FIG. 25) which accommodate adjustable, threaded compression rods 456, 458. Compression rods 456,458 are acted upon by one or more Belleville washers 460, 462 (or other suitable biasing means) to provide additional clamping force for locking clamping assemblies 416, 418 to rotor 404 when PZA's 424, 426 are de-energized. Adjustment of the force is provided by making up or backing off the threaded compression rods 456, 458. Of course, other structures may easily be adapted to provide additional clamping force, if desired or required by the application of the motor.

As with the finger motor, the appropriate timing of the clamping and release modes of clamping assemblies 416, 418 in combination with the timed energization of one or more PZA's employed in one or more drive assemblies 436, 438 will result in rotation of rotor 404 when a clamping assembly which is released by its PZA to grip rotor 404 is rotated by a drive PZA 442.

Described another way, the ratchet motor with two drive PZA's operates in a fashion similar to a familiar exercise for strengthening the wrists. In this exercise, a section of a broom handle is used with a rope fastened to the center of the handle and a weight attached to the other end of the rope. The exercise consists of grasping an end of the broom handle in each hand and turning it in order to lift the weight by winding up the rope on the broom handle. This is achieved through the following sequence of events.

1. Tightening the grasp of the right hand while releasing the left hand's grip.

2. Rolling the right wrist backward, toward the body.

3. Tightening the grasp of the left hand while releasing the right hand's grip.

4. Rolling the left wrist backward while rolling the right wrist forward, back to its original position in step 1.

The alternative clamping, rotating, releasing, and returning action is repeated the requisite number of times. Rotary motion in the opposite direction is simply achieved by reversing the phasing of the grasps.

Control circuitry for driving ratchet motor 400 is similar to that employed in the finger motor, and again may be easily fabricated from commercially available integrated circuit components by one of ordinary skill in the art. The drive signals, as with the finger motor, may be square, rectangular, triangular or other suitable waves, appropriately timed. As with the finger motor, the clamping PZA's are either energized or de-energized, and do not require any particular signal.

Suitable materials for the ratchet motor have also been previously discussed, and so will not be reiterated. The PZA's may be of the type previously described, sized to accommodate the desired force and rapidity of movement.

It has been previously noted that certain embodiments of the invention, when incorporated into various structures such as robotic hands, limbs, etc. may be made to become flexible or "go limp" upon de-energization. Such a capability is contemplated for all of the illustrated embodiments, and others, of the invention, just as is the ability to lock motor segments or components in position and to cause the structure to go rigid upon energization of actuators, for the purpose of clamping, locking or braking, as appropriate to the application of the motor.

D. Other Variations and Applications

Figures 33A, 33B, 33C:
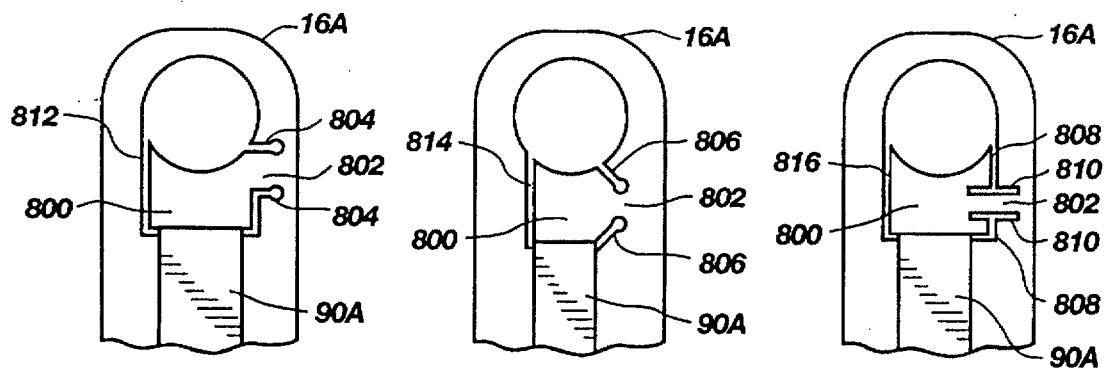
FIGS. 33A, 33B and 33C are partial side elevations of finger motor clamping subsegments employing integral clamping shoe elements.

A further refinement of the finger motor previously described herein is depicted in FIGS. 33A, 33B and 33C of the drawings. In lieu of a discrete clamping shoe component in an oscillating clamping structure such as 78A (see FIG. 4), a subsegment such as 16A may be structured to include an integral clamping shoe element 800 which is flexibly secured to the main body of subsegment 16A via neck portions 802, the degree and range of flexibility being alterable by the designer by selection of appropriate neck width and length and the length, width and configuration of slots such as 804, 806, 808 and 810 defining neck portions 802, as well as those of slots such as 812, 814 and 816 which provide some clearance for movement of clamping shoe elements 800 when acted upon by a PZA such as 90A.

Figure 34:
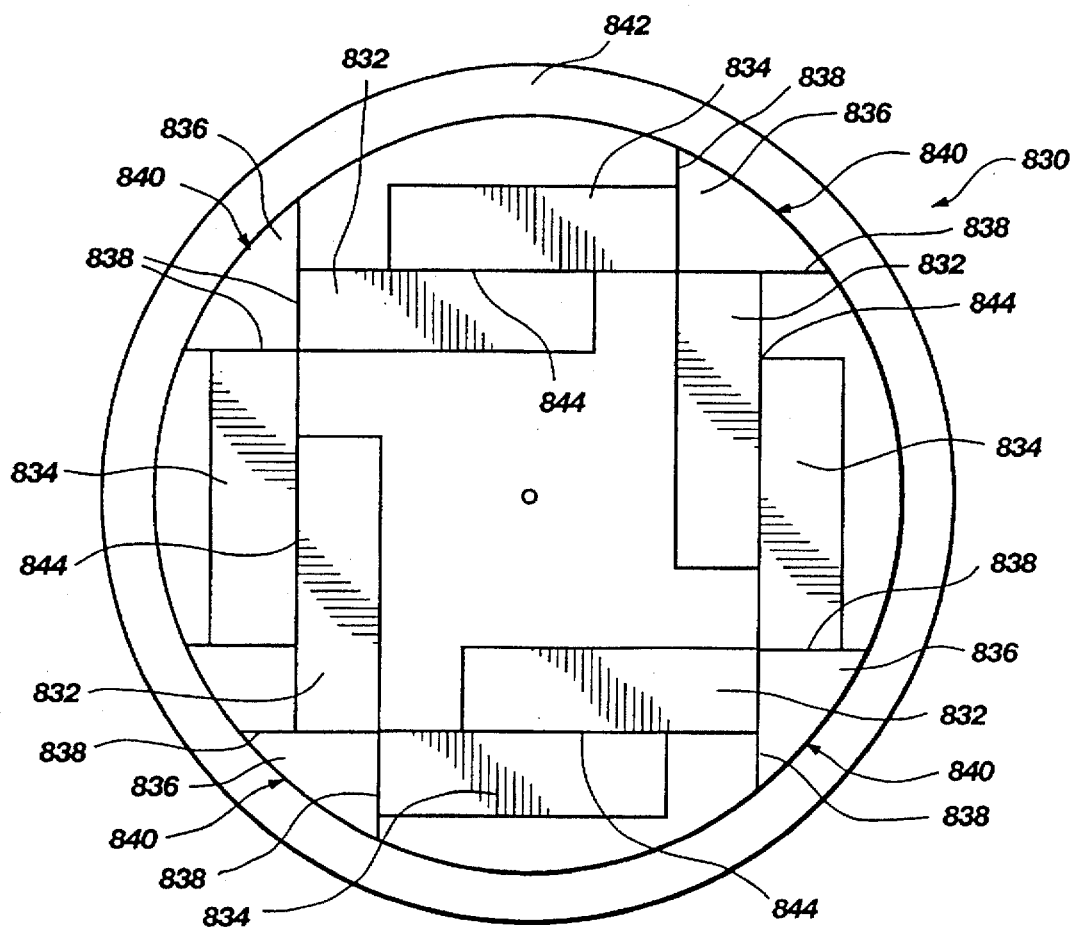
FIG. 34 is a schematic side elevation of a compact V-drive rotary star motor according to the present invention.

FIG. 34 depicts a compact or "dense" version 830 of a star motor, such as has previously been described with respect to FIGS. 15 and 16. Such a motor may be further described as an "V-drive" rotary star motor, the design advantages of which have been previously alluded to. Such a design may have particular utility in the design of a rotational joint for a robotic limb, such as a thigh joint or elbow or forearm joint. Motor 830 includes a plurality of overlapping paired PZA's 832 and 834 disposed at mutual included 90 degree angles, each PZA pair acting upon a generally triangular drive shoe 836 which offers two flat load faces 838 at 90 degree angles, and a third arcuate surface 840 which engages the I.D. of a rotor 842 which surrounds the drive assembly stator housing (not shown) in which the PZA's 832, 834 and drive shoes 836 are carried. Also not shown is a means as previously and subsequently described for biasing drive shoes 836 away from rotor 842 when PZA's are not energized. When PZA's 832 and 834 are selectively energized in the manner previously described with respect to FIGS. 12 and 12A, drive shoes 836 are moved to engage and disengage rotor 842 to cause rotation of same. A Teflon septum may be employed between laterally abutting PZA's at some or all of locations 844, in order to reduce friction therebetween as the PZA's expand and contract. As previously noted with respect to the other star motor embodiments, the PZA pairs may all be energized in phase, or sequentially, to provide a smoother and more continuous movement of rotor 842. It may also be observed that the terms rotor and stator are relative, and it may be that in certain applications the housing containing the PZA's and drive shoes may be caused to rotate while the "rotor" 842 remains stationary. While this would not normally be the case, due to the wiring required to drive and control the motor, such an arrangement is entirely within the contemplation of the inventor, particularly if only a limited range of arcuate motion is required.

Further, and most particularly in conjunction with the above- and previously-described V-drive and L-drive motors, the inventor has developed an alternate actuator drive sequencing which permits the motors previously described as low-speed, high-force or torque motors to operate in a high-speed, relatively low-force or torque mode. The previously-described actuator sequencing of FIGS. 12 and 12A may be described as the high-force mode, wherein the drive signal frequency may be up to about 5 kHz. In the high-speed mode, the drive signal frequency can be much higher, for example at least about 10 kHz, and actuator energizing and sequencing quite different. Specifically, with a V-drive motor, only the PZA driving the drive shoe in the desired direction is energized, the other PZA being maintained at a constant length and not performing any drive function. Thus, the driving direction PZA acts only in combination with the tensioning or other drive shoe biasing mechanism to move the rotor in the desired direction. The high frequency of the drive signal and attendant high frequency of contact by the drive shoe with the rotor substantially precludes the rotor from "backsliding" between drive strokes of the drive shoe in the desired direction. To reverse direction, the first PZA is idled, so to speak, and the opposing PZA driven at the aforementioned high frequency. While the high frequency drive signal and selective energizing of PZA's only in the driving direction has particular appeal with the V-drive star motors, such approach may also be adapted to L-drive and parallel-drive motors and at least to certain finger motor drive arrangements, as previously described. Any desired or required structural modifications to such motors for higher operating efficiency in the high speed mode will be apparent to one of ordinary skill in the art from the previously disclosed embodiments thereof and the above description of the manner in which the PZA's of the motors of the invention may driven for high speed operation.

FIG. 35 is a more detailed illustration of a structure depicted in FIG. 23, wherein it was suggested that the rotor element might comprise a flexible strip or band. FIG. 35 depicts a structure including two banks of actuators 850, each including sixteen actuators A paired to drive eight drive shoes D. The "rotor" in this instance comprises four stainless steel cables 852 paired in mutually parallel orientation, two per each bank 850 of actuators. As shown, cables 852 are secured to driven rotary elements 854 via tensioning bolt assemblies 856. Rotary elements 854 may be mounted on roller bearings 858, or other suitable bearing means as known in the art, which are secured to supporting housing 860.

FIGS. 36 and 37 schematically depict a compact linear motor 870 which includes actuator-driven clamping and drive assembly elements. Motor 870 includes a frame 872 which carries bushings 874 at each end thereof, the bushings slidably supporting drive rod 876 for movement in the axial directions 878. Pairs of mutually-perpendicularly oriented clamp actuators 880 act on drive shoes 882, drive shoes 882 having inner arcuate surfaces of substantially the same radius as that of the exterior of drive rod 876. Drive shoes 882 are disposed in two groups of four drive shoes each, one group proximate each end of frame 872. Clamp actuators 880 abut support posts 884 at the corners of frame 872, extending at the aforesaid mutually perpendicular orientations to seat in sockets 886 in drive shoes 882. Drive shoes 882 are mutually biased away from one another and so are, as a group of four, radially outwardly biased due to the interposition of a spring means 888 at their mutually abutting ends. The spring means 888 may comprise coil springs, belleville springs, resilient elastomeric elements or other means known in the art. Alternatively, or supplementally, tension springs (not shown) as previously described may be used to pull drive shoes 882 radially outwardly toward support posts 884. Eight drive actuators 890, four disposed for movement in each longitudinal direction, abut transversely-oriented center drive supports 892 as shown. In operation, one group of clamp actuators 880 is energized to cause the corresponding group of drive shoes 882 to grip the exterior of drive rod 876, after which the drive actuators 890 which abut those drive shoes 882 are energized and caused to expand, moving drive rod 876 a distance equal to the drive actuator longitudinal expansion in the desired direction. The other group of clamp actuators 880 is then energized to cause those drive shoes to grip the drive rod 876 to prevent movement, and the first group of clamp and drive actuators is then de-energized, causing the drive shoes to be reset for another drive cycle. To move drive rod 876 in the opposite direction, the actuator energizing cycle is suitably altered. While not shown in the drawing figures, it may be desirable to place longitudinal biasing means between the bushings 874 and the drive shoes 882 at locations 894 to facilitate the return of the drive shoes 882 to their rest or reset position. Such biasing means may be of the type previously described, or any others as known in the art. It may also be desirable to cover the support post-ends of clamp actuators 880 with teflon, to assist sliding movement thereof in the longitudinal direction when the drive shoes 882 are returned to rest position.

Figure 38:
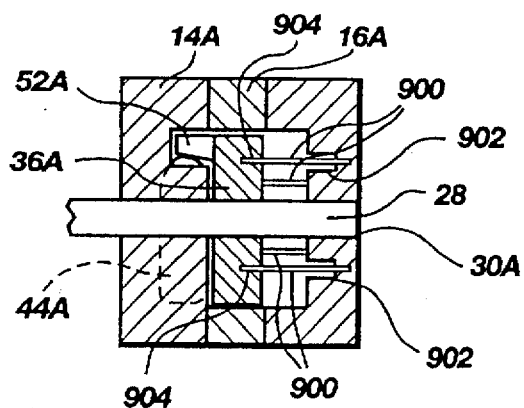
FIGS. 38 and 39 comprise, respectively, a partial sectional end elevation and a side elevation of a finger motor segment employing resilient wires for biasing a drive bushing.
Figure 39:
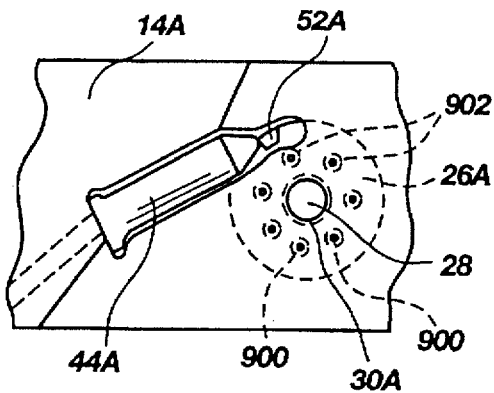

Yet another modification to the previously-described finger motor design involves the use of spring-steel music wire for torsional biasing of rotary drive elements such as a bushing 26A in lieu of a resilient return member such as 48A. As depicted in FIGS. 38 and 39, the fast ends of a plurality of resilient wires 900 extend into and are secured at the bottoms of the counterbores 902 in a finger segment such as 14A (shown in modified form), and are circumferentially spaced about pin receptacle 30A which receives the end of pin 28 about which element 26A rotates. The wires 900 extend longitudinally in the direction of pin 28, into cooperating apertures 904 in bushing 26A. When a drive actuator such as 44A is energized and elongates to move bushing 26A via drive pin 52A, wires 900 will be elastically deformed in the manner of cantilever beams as the bushing 26A moves arcuately about pin 28. When drive actuator 44A is de-energized, the spring force of the wire "beams" 900 will cause the bushing 26A to return to its rest position in anticipation of another cycle.

Figure 40:
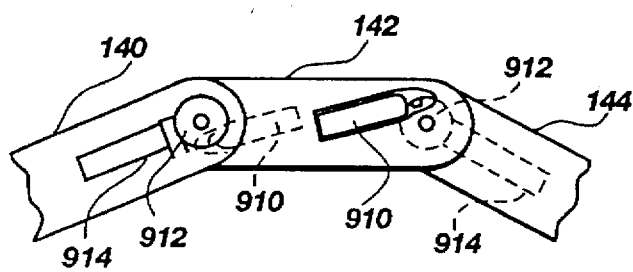
FIG. 40 comprises a multi-segment finger arrangement employing multiple drive actuator assemblies on the middle or proximal segment and clamping actuator assemblies on the basal and distal segments.

As shown schematically in drawing FIG. 40, it is also contemplated that a finger motor segment, such as the middle or proximal segment 142 of a three-segment finger (see also FIG. 7), may employ two drive actuators 910 and associated bushings 912, one actuator assembly acting on the basal segment 140 of the finger and the other on the distal segment 144. The wire drive-biasing structure of FIGS. 38 and 39 is particularly suitable for such an application due to it compactness. In such a case, the clamping actuator assemblies 914 would be placed on the basal and distal segments 140, 144 to act upon bushings 912.

Insofar as the operation of the motors of the present invention in its various embodiments, it has been recognized by the inventor that large temperature fluctuations and (over an extended period) wear of components such as drive shoes and rotors may cause the motors to lose efficiency. As a result, one additional subtle but yet significant aspect of the invention is to employ a base D.C. bias voltage to control the length of an actuator to compensate for ambient temperature or for temperature increases caused by protracted operation of the motor. In addition, as a drive shoe or rotor wears, the bias voltage may be increased to provide maintenance of proper tolerances.

Figure 41:
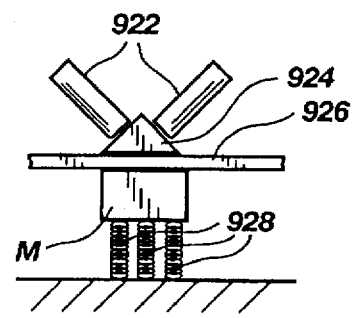
FIG. 41 is a schematic side elevation of a linear V-drive star motor employing a large mass in combination with spring pre-loading for biasing a rotor against a drive shoe.

Another manner of compensation for temperature fluctuations and wear in a motor assembly is schematically shown in FIG. 41 with respect to a V-drive linear motor 920, although the concept may be adapted to other configurations. Motor 920 includes two actuators 922 driving a triangular drive shoe 924, drive shoe 924 being biased upwardly (not shown) as previously discussed, away from linear rotor 926. Opposite drive shoe 924, a relatively large mass M substantially greater than the mass of the drive shoe 924 is biased by springs 928 against the lower surface of rotor 926. Springs 928 may comprise, coil, leaf, belleville or other suitable spring or an alternative biasing means, such as an elastomer, all as well known in the art. Thus, rotor 926 is pre-loaded against drive shoe 924, and the size of the mass M slows its potential movement under the urging of springs 928 to far less than the cycle times of drive shoe 924 so that the drive shoe 924 can move into and out of contact with the rotor 926 and move rotor 926 in the desired direction.

Figure 42:
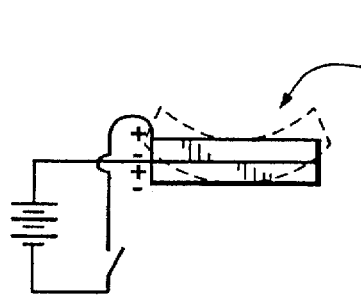
FIG. 42 is a schematic side elevation of a bending PZA with power supply.

It is also apparent that linear piezoelectric and other field actuators (PZA's) which are configured to bend or bow when energized, as previously referenced, may be employed in the construction of motors according to the present invention. Such a structure, with a schematic energizing circuit, is illustrated in FIG. 42. As shown, the linear structure 940 may be a laminate of two PZA's, which we will call a "bimorph PZA" for the sake of convenience. When the bimorph PZA 940 is energized, it bends or bows into an arcuate shape (shown in broken lines) as the upper PZA contracts in length and the lower PZA expands. This movement may be employed to rotate a shaft via a number of different connecting and power structures. It is also contemplated that a single PZA may be laminated to a resilient plate, rod or other elongated spring member to form a structure which bends or bows in a manner similar to a bimorph PZA. In this latter structure, energization and expansion of the PZA will cause the resilient member to bend, and de-energization of the PZA will result in the energy stored in the bowed spring member causing the laminated assembly to straighten.

Figure 43:
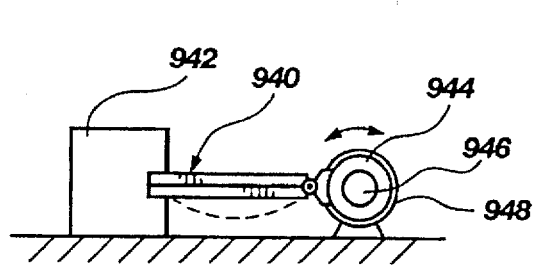
FIG. 43 is a schematic side elevation of a rotational shaft drive structure employing a bending PZA in combination with tubular PZA clamps.

FIG. 43 illustrates one exemplary structure employing a bimorph PZA or other similarly-acting bending actuator structure. Bimorph PZA 940 is substantially rigidly fixed at one end to a (relatively) immovable structure 942. The other end of PZA 940 is pivotally secured to a tubular PZA clamp 944 as known in the art, which PZA clamp 944 surrounds a shaft 946 to be rotationally driven. Ideally, the pivotal connection also provides some longitudinal flexibility or resiliency between the end of PZA 940 and tubular PZA clamp 944, to facilitate rotation of tubular PZA clamp 944 as PZA 940 bends. The connection may comprise a hinge in combination with a longitudinal spring element, or comprise a flexible and longitudinally resilient element such as a reinforced elastomer. A second tubular PZA clamp 948, shown in broken lines, is supported by a bracket fixed to a relatively (with respect to the shaft) immovable object. In operation, PZA clamp 944 is energized to reduce in internal diameter to clamp bimorph PZA 940 to shaft 946, after which bimorph PZA 940 is energized to bow (see broken lines), which bowing rotates shaft 946 in a counter-clockwise direction. Upon reaching its maximum arcuate displacement, tubular PZA clamp 948 is energized to fix shaft 946 in its new rotational position, while PZA clamp 944 and then bimorph PZA 940 are de-energized sequentially and return to their original positions. This sequence is then repeated to effect an additional increment of rotation. If desired, a plurality of bimorph (or other bending actuator) PZA drives may be employed for higher speeds or more torque, depending upon how the bimorphs are phased.

FIG. 44 depicts the shaft end of a bimorph or other bending PZA 940 in an arrangement similar to that of FIG. 43, but in lieu of a tubular PZA clamp 944, a split-ring PZA clamping structure 950 as illustrated and described in detail previously with respect to the ratchet motor of FIGS. 25 and 26 of the drawings is employed. Clamping structure 950 is pivotally secured to the free end of bending PZA 940, and as with the embodiment of FIG. 44, preferably with a pivotal connecting structure which also affords some longitudinal give or flexibility. A second clamp 952 to secure shaft 946 in position may also be of the split-ring type. Operation of such an assembly will obviously be similar to that of the assembly of FIG. 43.

Yet another application of a bending-type actuator drive system 960 is shown in FIG. 45. System 960 includes an outer stator housing 962, illustrated as circular, concentric with an inner clamping sleeve 964 which may be a tubular PZA structure or a split-ring structure as described previously to selective effect a connection with a shaft 946 extending therethrough. A plurality of circumferentially-spaced radially-extending drive spokes 966 extend inwardly from housing 962 to clamping sleeve 964 and are affixed to both. Drive spokes 966 are preferably comprised of a resilient element 968 elastically deformable in bending, such as spring steel in the form of a strap or thin beam. Affixed to each element 968 is least one PZA 970, and preferably two such PZA's, one on each side of resilient element 968, to effect selective bending thereof in response to energization of the PZA's. Thus, drive spokes 966 may be said to preferably comprise a bimorph PZA with a resilient center element. In operation, the PZA's of the drive spokes are energized after clamping sleeve 964 is energized to secure drive spokes 966 to shaft 946. Depending on the polarity of the voltage applied to the PZA's, drive spokes 966 are caused to bend in one direction or the other, thus incrementally rotating clamping sleeve 964 and shaft 946 in the desired direction. When the increment of rotation has been completed, shaft 946 is gripped by another clamping structure (not shown) as described with respect to other embodiment of the invention to fix it in place, and clamping sleeve 964 and drive spokes 966 are de-energized to return to their rest positions in anticipation of another power "bend". Of course, a series of drive spoke assemblies and clamping sleeves may be placed along shaft 946 to provide higher speed or more torque, depending upon phasing. In such an instance, it may be possible to eliminate a clamping structure which merely serves to immobilize the shaft after an increment of rotation as the drive spokes 966 are reset.

FIG. 46 depicts an application of a stack-type PZA to achieve an end result similar to that of the bimorph PZA's of FIGS. 42–44. Drive structure 980 employs at least one stack-type or conventional PZA 982 disposed at one end of a drive rod 984, PZA 982 opposed by either a biasing structure such as a spring 986 (belleville, coil, elastomeric, etc.) or another PZA 982. The other end of drive rod 984 is shown to be secured to a split-ring type clamping structure 988 encircling a shaft 946, although a tubular PZA clamp may also be employed. When it is desired to rotate shaft 946, clamping structure 988 is de-energized and PZA or PZA's 982 are appropriately energized to move drive rod 984 in the direction desired, transverse to the longitudinal axis of the rod. After the increment of rotation has been effected, clamping structure 988 is energized to release shaft 946, and the drive PZA 982 de-energized, return of rod 984 to its rest position being effected either by spring 986 or by energization of opposing PZA 982. Shaft 946 is maintained in its advanced rotational position by another suitable clamping structure affixed either to an immobile support or to another drive structure 980 disposed in tandem with the first.

Figure 47:
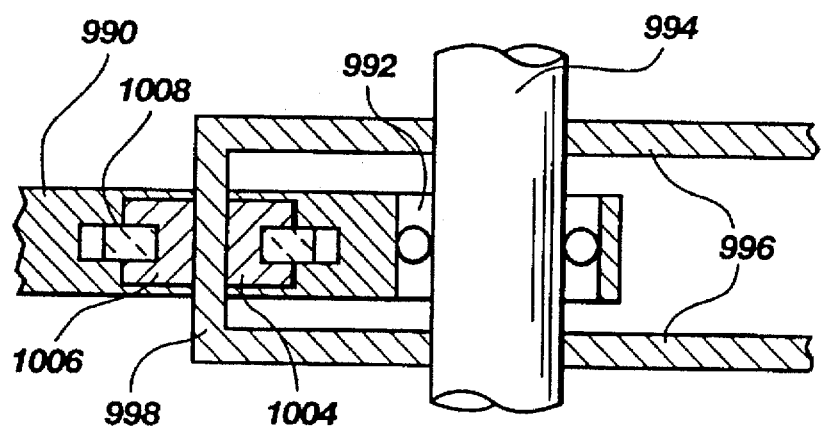
FIGS. 47 and 48 are, respectively, top and side elevations of a PZA-driven aircraft flap assembly segment.
Figure 48:
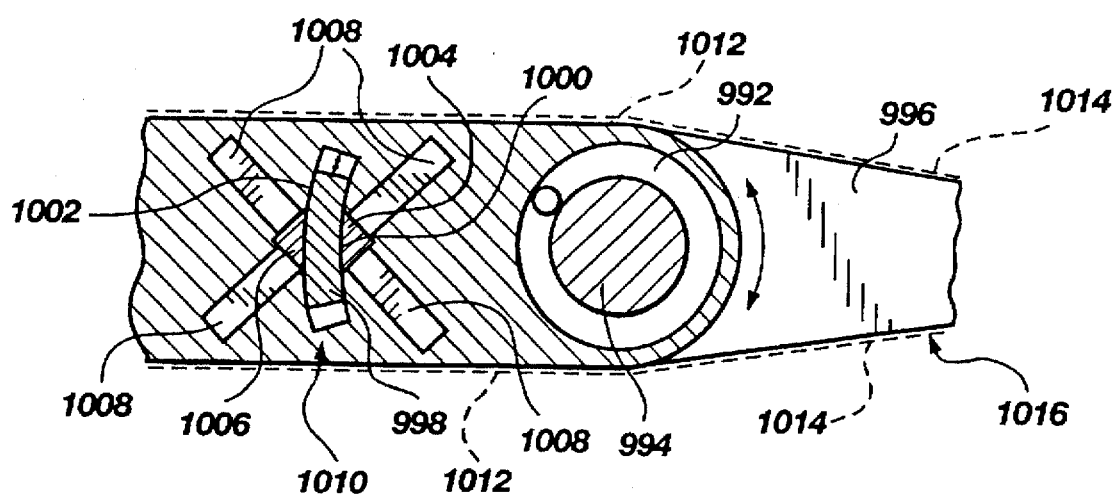

FIGS. 47 and 48 illustrate a first application of motors of the present invention to movement and control of movable flap surfaces for aircraft airfoils. As shown, a wing or other airfoil internal fixed support structure such as a rib 990 carries a bearing assembly 992 through which extends a shaft 994 to which are secured two parallel movable flap ribs 996 connected at their inner ends by a transversely-extending drive sector 998. Drive sector 998 includes a first and a second arcuate surface 1000 and 1002, respectively. Drive sector 998, in combination with inner and outer drive shoes 1004 and 1006, and a plurality of PZA's 1008, forms a double V-drive motor 1010. Tensioning members to bias drive shoes 1004 and 1006 away from drive sector 998 have not been shown, the structure and purpose of which having been previously described. It should be understood that shaft 994 extends through substantially the entire extent of the movable flap, and that a series of bearings, movable flap ribs and associated drive sectors and V-drives are distributed along the flap. It is further readily understood that the fixed ribs 990 and movable flap ribs 996 are covered with skins 1012 and 1014 of aluminum or other material (shown in broken lines for clarity) which comprise the airfoil and flap surfaces, as is known in the aircraft art. In operation, when it is desired to rotate a flap 1016 defined by a series of flap ribs 990 and skins 1014, PZA's 1008 are suitable energized to act upon drive shoes 1004 and 1006 in a manner previously described, drive sector 998 being moved in the manner of a linear rotor and thereby rotating flap 1016 and shaft 994 with respect to fixed ribs 990 via bearing assemblies 992. When it is desired to rotate flap 1016 in the opposite direction, the sequence of actuator energizing is reversed. When it is desired to immobilize flap 1016, all PZA's 1008 are energized to firmly hold the drive shoes against the drive sectors. Alternatively, other mechanisms such as solenoid- or hydraulically-actuated locking devices as known in the art may be employed to immobilize flap 1016. It is understood that trailing airfoil flaps are generally not locked or immobilized, but that leading flaps require a locking mechanism. In either instance, the present invention is suitable to provide flap adjustment and control.

An alternative approach to flap control is illustrated in FIGS. 49, 50 and 51. As with the preceding embodiment, a series of movable flap ribs 996 are secured to a shaft 994 which extends through a series of laterally-spaced bearing assemblies 992 which are carried by at least some of fixed ribs 990. However, in this structure, the drive for the flap 1016 is located at the ends of the flap, and comprises torsional resonant drivers 1020 as known in the art secured to the ends of shaft 994. As the drivers 1020 cause the shaft 994 to torsionally or rotationally vibrate back and forth in first a clockwise and then a counter-clockwise direction, PZA-driven damping structures 1022 on the fixed ribs 990 and on movable ribs 996 provide a manner to secure flap 1016 in a fixed position, or to sequentially couple and decouple flap 1016 to torsionally driven shaft 994 to rotate it for control purposes.

It should be noted that the shaft 994 is multiple wavelengths (of the torsional vibrations produced by drivers 1020) long, that fixed fibs 990 are placed at the oscillation nodes to avoid vibrational problems, and that the clamping structures 1022 on fixed ribs 990 and movable ribs 996 are placed one-half wavelength apart at the antinodes. The clamping structures 1022 may be configured as split ring clamps which are structured and cooperatively operate in the manner previously described with respect to the ratchet motor depicted in FIGS. 25 and 26 of the drawings to attain the desired positioning of movable ribs 996 with respect to torsionally oscillating shaft 994. As shown in FIGS. 50 and 51, shaft 994 may be configured with a slender center 1024 and a series of spaced struts 1026 having endplates 1028 arcuate clamping surfaces 1030 so as to provide a relatively high moment of inertia to the vibratory system with lower overall mass than a thick, solid round shaft. Moreover, clamping surface area on the arcuate outer surfaces 1030 may also be enhanced by the design as illustrated to reduce loading per unit of surface area.

FIGS. 52 and 53 illustrate an alternative V-drive motor configuration 1040 using a tubular spring or a belleville spring 1042 and a cradle-type support 1044 to bias drive shoe 1046 upwardly against actuators 1048. If desired, tolerances and/or spring force may be adjusted using a set screw 1050 arrangement as shown in FIG. 52.

FIGS. 54 and 55 illustrate a motor embodiment 1060 wherein two PZA's 1062 selectively move a drive shoe 1064 against the external surface 1066 of a sleeve 1068 rotationally mounted on a shaft 1070, while a transversely-oriented PZA 1072 moves the drive shoe 1069 tangentially to the sleeve. The first two PZA's 1062 are opposed by a spring 1074 or other biasing means which moves drive shoe 1064 away from sleeve 1068, while the transversely-oriented PZA 1072 is opposed by leaf spring 1076. The contact surface 1078 of drive shoe 1064 may be curved if desired to a radius slightly larger than the radius of the sleeve 1068 for better and more prolonged contact therewith during the drive cycle. This type of motor structure might also be employed for movable flaps for aircraft, for example if sleeve 1068 has a flap rib extending therefrom and, of course, a series of these motors are employed along the extent of the flap.

While the field actuator motors of the present invention have been described with reference to certain preferred and alternative embodiments, the invention is not so limited, and many additions, deletions and modifications will be apparent to those of ordinary skill in the art and may be implemented without departing from the spirit and scope of the invention as hereinafter claimed.

For example, many rotor element shapes may be employed, as well as rotor elements which are flexible in one or more planes. Actuators may be placed in side-by-side relationships to act upon larger drive shoe surfaces. Different types and shapes of field actuators may be combined in a single motor. Various embodiments of the motor of the present invention, and components thereof, may be combined in various ways to obtain yet other embodiments within the scope of the invention.

What is claimed is:

1. A motor, comprising:

a stator;

a T-shaped drive shoe having a head and a body, carried by said stator and including an arcuate exterior shaft contact surface on said head having a first radius of curvature;

two field actuators disposed between said stator and said drive shoe, flanking and substantially parallel to said drive shoe body and contacting said drive shoe head on each side of said body;

a first biasing element acting upon said drive shoe in opposition to said two field actuators;

at last a third field actuator oriented transversely to said two field actuators and disposed between said stator and said drive shoe;

a second biasing element acting upon said drive shoe in opposition to said at least a third field actuator; and a cylindrical, rotatable shaft having a second radius of curvature less than said first radius of curvature, adjacent said shaft contact surface of said drive shoe.

2. The motor of claim 1, wherein said second biasing element comprises a leaf spring.

3. The motor of claim 1, wherein said rotatable shaft is carried on an axle.

4. The motor of claim 1, wherein said rotatable shaft is oriented transversely with respect to said drive shoe contact surface.

5. A motor, comprising:

a stator;

a T-shaped drive shoe carried by said stator and including an exterior shaft contact surface;

two field actuators disposed between said stator and said drive shoe, flanking a body of said T and aligned substantially parallel thereto, and contacting a head of the T on each side of the body;

a first biasing element acting upon said drive shoe in opposition to said two field actuators;

at least a third field actuator oriented transversely to said two field actuators and disposed between said stator and said drive shoe;

a second biasing element acting upon said drive shoe in opposition to said at least a second field actuator; and a rotatable shaft adjacent said shaft contact surface of said drive shoe.

6. The motor of claim 5, wherein said second biasing element comprises a leaf spring.

7. The motor of claim 5, wherein said shaft is cylindrical in exterior cross-sectional profile, and said contact surface includes an arcuate portion, said arcuate portion having a radius of curvature greater than that of said shaft profile.

8. The motor of claim 5, wherein said rotatable shaft is carried on an axle.

9. The motor of claim 5, wherein said rotatable shaft is oriented transversely with respect to said drive shoe contact surface.

* * * * *

UNITED STATES PATENT AND TRADEMARK OFFICE
CERTIFICATE OF CORRECTION

PATENT NO : 5,726,520
DATED : March 10, 1998
INVENTOR(S) : Grahn

It is certified that error appears in the above-identified patent and that said Letters Patent is hereby corrected as shown below:

Column 1, line 21, after "specifically" insert a comma --,--;

Column 1, line 22, after "elements" insert a comma --,--;

Column 1, line 39, after "instances" insert a comma --,--;

Column 1, line 45, after "repulsion" insert a comma --,--;

Column 1, line 67, change "an" to --art--.

Column 2, line 31, after "inventor" insert a comma --,--;

Column 2, line 37, delete "for";

Column 2, line 63, after "may" insert a comma --,--;

Column 2, line 64, after "fact" insert a comma --,--;

Column 3, line 17, after "motor" insert a comma --,--;

Column 3, line 22, after "may" and "instances" insert a comma --,--;

Column 6, line 4, after "oscillating" and "herein" insert a comma --,--;

Column 6, line 8, after "dimension" insert a comma --,--;

Column 6, line 66, change "large" to --larger--;

Column 7, line 31, after "40A" insert a comma --,--;

Column 7, line 31, change "So" to --so--;

Column 9, line 27, after "generator" insert a comma --,--;

UNITED STATES PATENT AND TRADEMARK OFFICE
CERTIFICATE OF CORRECTION

PATENT NO  :  5,726,520
DATED      :  March 10, 1998
INVENTOR(S):  Grahn

It is certified that error appears in the above-identified patent and that said Letters Patent is hereby corrected as shown below:

Column 9, line 44, after "example" insert a comma --,--;

Column 9, line 50, after "actuators" and "type" insert a comma --,--;

Column 10, line 30, change "t0" and "t1" to --$t_0$-- and --$t_1$--, respectively;

Column 10, line 31, change "t0" to --$t_0$--;

Column 10, line 32, change "t1" to --$t_1$--;

Column 10, line 42, change "t1" to --$t_1$--;

Column 10, line 44, change "t1" (both occurrences) to --$t_1$-- (both occurrences);

Column 10, line 44, change "14" (both occurences) to --$t_4$-- (both occurrences);

Column 10, line 51, change "t2" to --$t_2$--;

Column 10, line 57, change "t2" to --$t_2$--;

Column 10, line 61, after "preferred" and "circumstances" insert a comma --,--;

Column 10, line 62, after "de-energized" insert a comma --,--;

Column 11, line 17, change "t2" and "t3" to --$t_2$-- and --$t_3$--, respectively;

Column 11, line 22, change "t3" to --$t_3$--;

Column 11, line 23, change "t3" to --$t_3$--;

Column 11, line 30, change "t3" to --$t_3$--;

Column 11, line 32, change "t4" to --$t_4$--;

Column 11, line 37, change "t4" to --$t_4$--;

Column 11, line 43, change "t4" to --$t_4$--;

Column 11, line 44, change "t5" to --$t_5$--;

Column 11, line 45, change "t8" to --$t_8$ --;

Column 11, line 46, change "t5" to --$t_5$--;

Column 11, line 46, change "t8" to --$t_8$--;

Column 11, line 54, change "t5" and "t6" to --$t_5$-- and --$t_6$--, respectively;

Column 11, line 55, after "counter-clockwise" insert a comma --,--;

Column 11, line 57, change "t6" to --$t_6$--;

Column 11, line 62, change "t6" to --$t_6$--;

UNITED STATES PATENT AND TRADEMARK OFFICE
CERTIFICATE OF CORRECTION

PATENT NO : 5,726,520
DATED : March 10, 1998
INVENTOR(S) : Grahn

It is certified that error appears in the above-identified patent and that said Letters Patent is hereby corrected as shown below:

Column 11, line 63, change "t7", "t6" and "t7" to --$t_7$--, --$t_6$--, and --$t_7$--, respectively;
Column 11, line 64, change "t7" to --$t_7$--;
Column 12, line 3, change "t7" to --$t_7$--;
Column 12, line 5, change "t8" to --$t_8$--;
Column 12, line 8, change "t8" to --$t_8$--;
Column 12, line 13, after "actuators" insert a comma --,--;
Column 12, lines 14 and 15, after "invention" insert a comma --,--;
Column 12, line 21, change "is" to --in--;
Column 12, line 47, after "10" insert a comma --,--;
Column 12, line 48, after "invention" insert a comma --,--;
Column 13, line 13, after "motor" insert a comma --,--;
Column 13, line 14, after "invention" insert a comma --,--;
Column 13, line 66, change "t1" to --$t_1$--;
Column 14, line 13, after "modified" insert a comma --,--;
Column 14, line 14, after "desired" insert a comma --,--;
Column 14, line 20, after "10" insert a comma --,--;
Column 14, line 21, after "drawings" insert a comma --,--;
Column 14, line 54, after "Thus" insert a comma --,--;
Column 14, line 59, after "may" and "instances" insert a comma --,--;
Column 15, line 3, after "Further" insert a comma --,--;
Column 15, line 5, after "rotation" (first occurrence) insert a comma --,--;
Column 15, line 6, after "arc" insert a comma --,--.
Column 15, line 19, change "serf-braking" to --self-braking--;
Column 15, line 38, after "268" insert a comma --,--;
Column 15, line 46, after "254" insert a comma --,--;
Column 16, line 7, change "simple" to --simply--;
Column 16, line 9, after "therewith" insert a comma --,--;

UNITED STATES PATENT AND TRADEMARK OFFICE
CERTIFICATE OF CORRECTION

PATENT NO : 5,726,520
DATED : March 10, 1998
INVENTOR(S) : Grahn

It is certified that error appears in the above-identified patent and that said Letters Patent is hereby corrected as shown below:

Column 16, line 11, after "250" insert a comma --,--;

Column 16, line 39, after "266" insert a comma --,--;

Column 16, line 40, after "272" insert a comma --,--;

Column 16, line 43, after "300" insert a comma --,--;

Column 16, line 44, after "260" insert a comma --,--;

Column 16, line 52, after "energized" insert a comma --,--;

Column 16, line 66, delete the first occurrence of "to";

Column 17, line 14, change "necessary" to --necessarily--;

Column 17, line 15, change "necessary" to --necessarily--;

Column 17, line 32, after "described" insert a comma --,--;

Column 17, line 52, after "phase" insert a comma --,--;

Column 17, line 56, change "drive" to --driven--;

Column 17, line 61, after "phasing" insert a comma --,--;

Column 18, line 12, after "addition" insert a comma --,--;

Column 18, lines 13-14, after "embodiment" insert a comma --,--;

Column 18, line 15, after "movement" insert a comma --,--;

Column 18, line 18, after "embodiment" insert a comma --,--;

Column 19, line 26, delete "a".

Column 19, line 29, after "example" insert a comma --,--;

Column 19, line 46, after "embodiment" insert a comma --,--;

Column 19, line 50, after "motor" insert a comma --,--;

Column 19, line 51, after "30" insert a comma --,--;

Column 20, line 4, after "motors" insert a comma --,--;

Column 20, line 18, after "400" and "invention" insert a comma --,--;

Column 20, line 33, after "therethrough" insert a comma --,--;

Column 20, line 56, after "442" insert a comma --,--;

Column 20, line 66, after "404" insert a comma --,--;

UNITED STATES PATENT AND TRADEMARK OFFICE
CERTIFICATE OF CORRECTION

PATENT NO : 5,726,520
DATED : March 10, 1998
INVENTOR(S) : Grahn

It is certified that error appears in the above-identified patent and that said Letters Patent is hereby corrected as shown below:

Column 21, line 2, after "phases" and "desired" insert a comma --,--;
Column 21, line 22, after "assembly" and "404" insert a comma --,--;
Column 22, line 2, after "motor" insert a comma --,--;
Column 22, line 7, after "800" insert a comma --,--;
Column 22, line 12, after "810" insert a comma --,--;
Column 22, line 13, after "816" insert a comma --,--;
Column 22, line 30, after "shown" and "means" insert a comma --,--;
Column 22, line 31, after "described" insert a comma --,--;
Column 23, line 24, after "actuators A" insert a comma --,--;
Column 23, line 25, after "rotor" and "instance" insert a comma --,--;
Column 23, line 51, change "belleville" to --Belleville--;
Column 23, line 53, after "(not shown)" and "described" insert a comma --,--;
Column 24, line 15, after "elements" insert a comma --,--;
Column 24, line 16, after "26A" insert a comma --,--;
Column 24, line 17, change "fast" to --first--;
Column 24, line 25, after "actuator" and "44A" insert a comma --,--;
Column 24, line 46, after "components" insert a comma --,--;
Column 24, line 47, after "rotors" insert a comma --,--;
Column 24, line 48, after "subtle" and "significant" insert a comma --,--;
Column 24, line 65, change "belleville" to --Belleville--;
Column 25, line 3, after "924" insert a comma --,--;
Column 25, line 45, change "fines" to --lines--;
Column 25, line 58, after "950" insert a comma --,--;
Column 25, line 59, after "previously" insert a comma --,--;
Column 25, line 60, after "drawings" insert a comma --,--;
Column 25, line 63, after "structure" insert a comma --,--;
Column 26, line 6, change "selective" to --selectively--;

UNITED STATES PATENT AND TRADEMARK OFFICE
CERTIFICATE OF CORRECTION

PATENT NO : 5,726,520
DATED : March 10, 1998
INVENTOR(S) : Grahn

It is certified that error appears in the above-identified patent and that said Letters Patent is hereby corrected as shown below:

Column 26, line 13, after "968 is" insert --at--;
Column 26, line 33, after "structure" insert a comma --,--;
Column 26, line 35, after "rotation" insert a comma --,--;
Column 26, line 41, after "structure" insert a comma --,--;
Column 26, line 41, change "belleville" to --Belleville--;
Column 26, line 42, after "etc.)" insert a comma --,--;
Column 27, line 11, after "clarity)" insert a comma --,--;
Column 27, line 24, after "devices" and "art" insert a comma --,--;
Column 27, line 37, after "1020" and "art" insert a comma --,--;
Column 27, line 41, change "damping" to --clamping--;
Column 27, line 53, after "clamps" insert a comma --,--;
Column 27, line 54, after "described" insert a comma --,--;
Column 27, line 60, after "1030" insert a comma --,--;
Column 27, line 67, change "belleville" to --Belleville--;
Column 28, line 5, after "1060" insert a comma --,--; and
Column 28, line 51, change "last" to --least--.

Signed and Sealed this

Twenty-fourth Day of October, 2000

Attest:

Attesting Officer

Q. TODD DICKINSON

Director of Patents and Trademarks